(12) United States Patent
Berger et al.

(10) Patent No.: US 9,293,717 B2
(45) Date of Patent: Mar. 22, 2016

(54) METHODS FOR PRODUCING SEMICONDUCTOR NANOPARTICLES

(75) Inventors: Bryan Berger, Doylestown, PA (US); Steven McIntosh, Allentown, PA (US)

(73) Assignee: Lehigh University, Bethlehem, PA (US)

( * ) Notice: Subject to any disclaimer, the term of this patent is extended or adjusted under 35 U.S.C. 154(b) by 0 days.

(21) Appl. No.: 14/239,175

(22) PCT Filed: Aug. 16, 2012

(86) PCT No.: PCT/US2012/051068
§ 371 (c)(1),
(2), (4) Date: Feb. 17, 2014

(87) PCT Pub. No.: WO2013/025868
PCT Pub. Date: Feb. 21, 2013

(65) Prior Publication Data
US 2014/0287483 A1    Sep. 25, 2014

Related U.S. Application Data

(60) Provisional application No. 61/524,126, filed on Aug. 16, 2011.

(51) Int. Cl.
| | | |
|---|---|---|
| *C12P 3/00* | (2006.01) | |
| *B82Y 40/00* | (2011.01) | |
| *H01L 51/00* | (2006.01) | |
| *B82B 3/00* | (2006.01) | |
| *B82Y 5/00* | (2011.01) | |

(52) U.S. Cl.
CPC .......... *H01L 51/0093* (2013.01); *B82B 3/0057* (2013.01); *B82Y 5/00* (2013.01); *C12P 3/00* (2013.01)

(58) Field of Classification Search
None
See application file for complete search history.

(56) References Cited

U.S. PATENT DOCUMENTS

| 7,060,473 | B2 | 6/2006 | Phelps et al. |
|---|---|---|---|
| 2010/0184179 | A1 | 7/2010 | Rondinone et al. |
| 2010/0193752 | A1 | 8/2010 | Phelps et al. |

OTHER PUBLICATIONS

Mandal et al. 2006.The use of microorganisms for the formation of metal nanoparticles and their application. Applied Microbiology and Biotechnology, vol. 69, pp. 485-492.*
Dameron et al. 1989. Biosynthesis of cadmium sulphide quantum semiconductor crystallites. NATURE, vol. 338, pp. 596-597, Apr. 13, 1989.*
Drancourt et al.1997. *Stenotrophomonas africana* sp. nov., an Opportunistic Human Pathogen in Africa. International Journal of Systematic Bacteriology, vol. 47, No. 1, pp. 160-163.*
Denton et al. 1998. Microbiological and Clinical Aspects of Infection Associated with Stenotrophomonas maltophilia. Clinical Microbiology Reviews, vol. 11, No. 1, pp. 57-80.*
Dameron et al.1989. Biosynthesis of cadmium sulphide quantum semiconductor crystallites. Nature, vol. 338. Apr. 13, 1989, pp. 596-597.*
Rai et al., Biogenic Nanoparticles: An Introduction to What They Are, How They Are Synthesized and Their Applications. Chapter 1, pp. 1-14, in M. Rai and N. Duran (eds.), Metal Nanoparticles in Microbiology, DOI 10.1007/978-3-642-18312-6_1, # Springer-Verlag Berlin Heidelberg 20, Published Mar. 4, 2011.*
Cunningham et al. 1993. Precipitation of Cadmium by Clostridium thermoaceticum. Applied and Environmental Microbiology, vol. 59, No. 1, pp. 7-14.*
Sweeney et al. 2004) Bacterial Biosynthesis of Cadmium Sulfide Nanocrystals. Chemistry &Biology, vol. 11, pp. 1553-1559.*
Nossal et al. 1966. The Release of Enzymes by Osmotic Shock from *Escherichia coli* in Exponential Phase. The Journal of Biological Chemistry, vol. 241, No. 13, pp. 3051-3062.*
Nangia et al. 2009.A novel bacterial isolate Stenotrophomonas maltophilia as living factory for synthesis of gold nanoparticles. Microbial Cell Factories, vol. 8, pp. 39-45 (1-7).*
T.J. Beveridge, 1978.. The response of cell walls of Bacillus subtilis to metals and to electron microscopic stains. Canadian Journal of Microbiology, vol. 24, pp. 89-104.*
1996-2012. Chemical Elements .Periodic Table at Chemical eelments.com.*
Kloepfer, J. A. et al. Uptake of CdSe and CdSe ZnS Quantum Dots in Bacteria via Purine-Dependent Mechanisms. Appl. Environ. Microbiol. May 2005, 1-35, vol. 71, No. 5, pp. 2548-2557. See pp. 2548, 2549, 2555, 2556. US.
International Search Report for PCT/US12/51068, filed Aug. 16, 2012. WO.
Berger, B. et al., "Green Chemistry, Cutting-edge research for a greener sustainable future." Royal Society of Chemistry; vol. 17, No. 7, Jul. 2015, pp. 3655-4090.

* cited by examiner

*Primary Examiner* — Debbie K Ware
*Assistant Examiner* — Kailash C Srivastava
(74) *Attorney, Agent, or Firm* — Blank Rome LLP

(57) ABSTRACT

New semiconductor nanoparticles and manufacturing technologies, including novel methods, systems, and compositions, are provided herein. Robust, reproducible production of large amounts of semiconductor nanoparticles, such as quantum dots, from bacterial cultures during continuous growth is provided, without a need for extensive post growth processing or modification. The result is a novel semiconductor of nanoparticle dimensions and quality that is suitable for commercial applications in lighting, display, imaging, diagnostics, photovoltaics and hydrogen generation, for example. In one embodiment, bacterial-based synthesis methods for producing nanocrystal semiconductor quantum dots are provided by aqueous, environmentally friendly media and methods.

11 Claims, 15 Drawing Sheets

Genotyping of environmental S. maltophilia isolate – Variant 5 (LHU-5-CP1)

TGCAGTCGAACGGCAGCACAGGAGAGCTTGCTCTCTGGGTGGCGAGTGGCGGACGGGTGAGGAATACATCGGA
ATCTACTTTTTCGTGGGGGATAACGTAGGGAAACTTACGCTAATACCGCATACGACCTACGGGTGAAAGCAGGGG
ATCTTCGGACCTTGCGCGATTGAATGAGCCGATGTCGGATTAGCTAGTTGGCGGGGTAAAGGCCCACCAAGGCGA
CGATCCGTAGCTGGTCTGAGAGGATGATCAGCCACACTGGAACTGAGACACGGTCCAGACTCCTACGGGAGGCA
GCAGTGGGGAATATTGGACAATGGGCGCAAGCCTGATCCAGCCATACCGCGTGGGTGAAGAAGGCCTTCGGGTT
GTAAAGCCCTTTTGTTGGGAAANAAANCCAGCNGGTTAANACCCGGTTGGGANGACGGTACCCNAAGAATAAGC
ACCNNCNANNTTCANGCCNNCA

Figure 12

Genotyping of environmental S. maltophilia isolate – Variant 5 (LHU-5-CP2)

CGTCNTCCCNACCGGGTATTAACCAGCTGGATTTCTTTCCCAACAAAAGGGCTTTACAACCCGAAGGCCTTCTTCAC
CCACGCGGTATGGCTGGATCAGGCTTGCGCCCATTGTCCAATATTCCCCACTGCTGCCTCCCGTAGGAGTCTGGAC
CGTGTCTCAGTTCCAGTGTGGCTGATCATCCTCTCAGACCAGCTACGGATCGTCGCCTTGGTGGGCCTTTACCCCGC
CAACTAGCTAATCCGACATCGGCTCATTCAATCGCGCAAGGTCCGAAGATCCCCTGCTTTCACCCGTAGGTCGTAT
GCGGTATTAGCGTAAGTTTCCCTACGTTATCCCCCACGAAAAAGTAGATTCCGATGTATTCCTCACCCGTCCGCCAC
TCGCCACCCAGAGAGCAAGCTCTCCTGTGCTGCCGTTCGACTTGCANGTGTTAGGCCTACCGCCAGCGTTCACTCT
NANCCAGGATCAANCTCTCCAA

Figure 13

Genotyping of environmental S. maltophilia isolate – Variant 4 (LHU-4-CP1)

NACNCNNGCAGTCGAACGGCAGCACAGGANAGCTTGCTCTCTGGGTGGCGAGTGGCGGNCGGGTGAGGAATAC
ATCGGAATCTACTTTTTCGTGGGGGATAACGTAGGGAAACTTACGCTAATACCGCATACGACCTACGGGTGAAAG
CAGGGGATCTTCGGACCTTGCGCGANTGAATGAGCCNATGTCGGANTANCNNNNNGGNGGGNNNNNNGNCCA
CCANNGC

Figure 14

Genotyping of environmental S. maltophilia isolate – Variant 4 (LHU-4-CP2)

TNNGGNNGTCNTCCCNACCGGGTATTAACCAGCTGGATTTCTTTCCCAACAAAAGGGCTTTACAACCCGAAGGCC
TTCTTCACCCACGCGGTATGGCTGGATCAGGCTTGCGCCCATTGTCCAATATTCCCCACTGCTGCCTCCCGTAGGAG
TCTGGACCGTGTCTCAGTTCCAGTGTGGCTGATCATCCTCTCAGACCAGCTACGGATCGTCGCCTTGGTGGGCCTTT
ACCCCGCCAACTAGCTAATCCGACATCGGCTCATTCAATCGCGCAAGGTCCGAAGATCCCCTGCTTTCACCCGTAG
GTCGTATGCGGTATTAGCGTAAGTTTCCCTACGTTATCCCCCACGAAAAAGTAGATTCCGATGTATTCCTCACCCGT
CCGCCACTCGCCACCCAGAGAGCAAGCTCTCCTGTGCTGCCGTTCGACTTGCATGTGTTAGGCCTACCGCCAGCGT
TCACTCTGAGCNAGGATCAAACTCTCCAAN

Figure 15

Genotyping of environmental S. maltophilia isolate – Variant 3 (LHU-3-CP1)

NCNTGCAGTCGNCGGCAGCACAGGAGAGCTTGCTCTCTGGGTGGCGAGTGGCGGACGGGTGAGGAATACATCG
GAATCTACTTTTTCGTGGGGGATAACGTAGGGAAACTTACGCTAATACCGCATACGACCTACGGGTGAAAGCAGG
GGATCTTCGGACCTTGCGCGATTGAATGAGCCGATGTCGGATTAGCTAGTTGGCGGGGTAAAGGCCCACCAAGGC
GACGATCCGTAGCTGGTCTGAGAGGATGATCAGCCACACTGGAACTGAGACACGGTCCAGACTCCTACGGGAGG
CAGCAGTGGGGAATATTGGACAATGGGCGCAAGCCTGATCCAGCCATACCGCGTGGGTGAAGAAGGCCTTCGGG
TTGTAAAGCCCTTTTGTTGGGAAAGAAATCCAGCTGGTTAATACCCGGTTGGGATGACGGTACCCAAAGAATAAG
CACCGGCTAACTTCNNGCCAGCNNNNNCGGTAATANANNTTNT

Figure 16

Genotyping of environmental S. maltophilia isolate – Variant 3 (LHU-3-CP2)

TCNTCCCNACCGGGTATTAACCAGCTGGANTTCTTTCCCAACAAAAGGGCTTTACAACCCGAAGGCCTTCTTCACC
CACGCGGTATGGCTGGATCAGGCTTGCGCCCATTGTCCAATATTCCCCACTGCTGCCTCCCGTAGGAGTCTGGACC
GTGTCTCAGTTCCAGTGTGGCTGATCATCCTCTCAGACCAGCTACGGATCGTCGCCTTGGTGGGCCTTTACCCCGCC
AACTAGCTAATCCGACATCGGCTCATTCAATCGCGCAAGGTCCGAAGATCCCCTGCTTTCACCCGTAGGTCGTATG
CGGTATTAGCGTAAGTTTCCCTACGTTATCCCCCACGAAAAAGTAGATTCCGATGTATTCCTCACCCGTCCGCCACT
CGCCACCCAGAGAGCAAGCTCTCCTGTGCTGCCGTTCGACTTGCATGTGTTAGGCCTACCGCCAGCGTTCACTCTN
ANCCNNGANCAAACTCTCCN

Figure 17

Genotyping of environmental S. maltophilia isolate – Variant 2 (LHU-2-CP1)

CNTGCNAGTCGAACGGCAGCACAGGAGAGCTTGCTCTCTGGGTGGCGAGTGGCGGACGGGTGAGGAATACATC
GGAATCTACTTTTTCGTGGGGGATAACGTAGGGAAACTTACGCTAATACCGCATACGACCTACGGGTGAAAGCAG
GGGATCTTCGGACCTTGCGCGATTGAATGAGCCGATGTCGGATTAGCTAGTTGGCGGGGTAAAGGCCCACCAAG
GCGACGATCCGTAGCTGGTCTGAGAGGATGATCAGCCACACTGGAACTGAGACACGGTCCAGACTCCTACGGGA
GGCAGCAGTGGGGAATATTGGACAATGGGCGCAAGCCTGATCCAGCCATACCGCGTGGGTGAAGAAGGCCTTCG
GGTTGTAAAGCCCTTTTGTTGGGAAAGAAATCCAGCTGGTTAATACCCGGTTGGGATGACGGTACCCAAAGAATA
AGCACCGGCTAACTTCNNGCCAGCNNNNNNGGTAAT

Figure 18

Genotyping of environmental S. maltophilia isolate – Variant 2 (LHU-2-CP2)

GTCNTCCCNACCGGGTATTAACCAGCTGGATTTCTTTCCCAACAAAAGGGCTTTACAACCCGAAGGCCTTCTTCACC
CACGCGGTATGGCTGGATCAGGCTTGCGCCCATTGTCCAATATTCCCCACTGCTGCCTCCCGTAGGAGTCTGGACC
GTGTCTCAGTTCCAGTGTGGCTGATCATCCTCTCAGACCAGCTACGGATCGTCGCCTTGGTGGGCCTTTACCCCGCC
AACTAGCTAATCCGACATCGGCTCATTCAATCGCGCAAGGTCCGAAGATCCCCTGCTTTCACCCGTAGGTCGTATG
CGGTATTAGCGTAAGTTTCCCTACGTTATCCCCCACGAAAAAGTAGATTCCGATGTATTCCTCACCCGTCCGCCACT
CGCCACCCAGAGAGCAAGCTCTCCTGTGCTGCCGTTCGACTTGCATGTGTTAGGCCTACCGCCAGCGTTCACTCTN
NNNCNNGATCNNACTCTCCAAAA

Figure 19

Genotyping of environmental S. maltophilia isolate – Variant 1 (LHU-1-CP1)

NNTGCAGTCGAACGGCAGCACAGGAGAGCTTGCTCTCTGGGTGGCGAGTGGCGGACGGGTGAGGAATACATCG
GAATCTACTTTTTCGTGGGGGATAACGTAGGGAAACTTACGCTAATACCGCATACGACCTACGGGTGAAAGCAGG
GGATCTTCGGACCTTGCGCGATTGAATGAGCCGATGTCGGATTAGCTAGTTGGCGGGGTAAAGGCCCACCAAGGC
GACGATCCGTAGCTGGTCTGAGAGGATGATCAGCCACACTGGAACTGAGACACGGTCCAGACTCCTACGGGAGG
CAGCAGTGGGGAATATTGGACAATGGGCGCAAGCCTGATCCAGCCATACCGCGTGGGTGAAGAAGGCCTTCGGG
TTGTAAAGCCCTTTTGTTGGGAAAGAAATCCAGCTGGTTAATACCCGGTTGGGATGACGGTACCCAAAGAATAAG
CACCGGCTAACTNNNTGCNANNNGCCNNNGTAATNN

Figure 20

Genotyping of environmental S. maltophilia isolate LU08

GGGATAACGTAGGGAAACTTACGCTAATACCGCATACGACCTACGGGTGAAAGCAGGGGATCTACGGACCTTGC
GCGATTGAATGAGCCGATGTCGGATTAGCTAGTTGGCGGGGTAAAGGCCCACCAAGGCGACGATCCGTAGCTGG
TCTGAGAGGATGATCAGCCACACTGGAACTGAGACACGGTCCAGACTCCTACGGGAGCCAGCAGTGGGGAATAT
TGGACAATGGGCGCAAGCCTGATCCAGCCATACCGCGTGGGTGAAGAAGGCCTTCGGGTTGTAAAGCCCTTTTCT
TGGGAAAGAAATCCAGCTGGTTAATACCCGGTTGGGATGACGGTACCCAAAGAATAAGCACCGGCTAACTTCGTG
CCAGCAGCCGCGGTAATACGAAGGGTGCAAGCGTTACTCGGAATTACTGGGCGTAAAGCGTGCGTAGGTGGTTG
TTTAAGTCTGTTGTGAAAGCCCTGGGCTCAACCTGGGAACTGCAGTGGAAACTGGACGACTAGAGTGTGGTAGAG
GGTAGCGGAATTCCTGGTGTAGCAGTGAAATGCGTAGAGATCAGGAGGAACATCCATGGCGAAGGCAGCTACCT
GGACCAAGACTGACACTGAGGCACGAAAGCGTGGGGAGCAAACAGGATTAGATACCCTGGTAGTCCACGCCCTA
AACGATGCGAACTGGATGTTGGGTGCAATTTGGCACGCAGTATCGAAGCTAACGCGTTAAGTTCGCCGCCTGGGG
AGTACGGTCGCAAGACTGAAACTCAAAGGAATTGACGGGGGCCCGCACAAGCGGTGGAGTATGTGGTATAATTC
GATGCAACGCGAAGAACCTTACCTGGCCTTGACATCTCGAGAACTTTCCAGAGATGGATTGGTGCCTTCGGGAACT
CGAACACAGGTGCTGCATGGCTGTCGTCAGCTCGTGTCGTGAGATGTTGGGTTAAGTCCCGCAACGAGCGCAACC
CTTGTCCTTAGTTGCCAGCACGTAATGGTGGGAACTCTAAGGAGACCGCCGGTGACAAACCGGAGGAAGGTGGG
GATGACGTCAAGACATCATGGCCCTTACGGCCAGGGCTACACACGTACTACAATGGTAGGGACAGAGGGCTGCA
AGCCGGCGACGGTAAGCCAATCCCAGAAACCCTATCTCAGTCCGGATTGGAGTCTGCAACTCGACTCCATGAAGT
CGGAATCGCTAGTAATCGCAGATCAGCATTGCTGCGGTGAATACGTTCCCGGGCCTTGTACACACCGCCCGTCACA
CCATGGGAGTTT

F1; AGAGTTTGATCCTGGCTCAG

R1; GGTTACCTTGTTACGACTT

Figure 21

SEQUENCE LISTING

```
<160> NUMBER OF SEQ ID NOS: 13

<210> SEQ ID NO 1
<211> LENGTH: 1278
<212> TYPE: DNA
<213> ORGANISM: Stenotrophomonas maltophilia

<400> SEQUENCE: 1
gggataacgt agggaaactt acgctaatac cgcatacgac ctacgggtga aagcagggga      60
tctacggacc ttgcgcgatt gaatgagccg atgtcggatt agctagttgg cggggtaaag     120
gcccaccaag gcgacgatcc gtagctggtc tgagaggatg atcagccaca ctggaactga     180
gacacggtcc agactcctac gggagccagc agtggggaat attggacaat gggcgcaagc     240
ctgatccagc cataccgcgt gggtgaagaa ggccttcggg ttgtaaagcc cttcttggga     300
aagaaatcca gctggttaat acccggttgg gatgacggta cccaaagaat aagcaccggc     360
taacttcgtg ccagcagccg cggtaatacg aagggtgcaa gcgttactcg gaattactgg     420
gcgtaaagcg tgcgtaggtg gttgtttaag tctgttgtga aagccctggg ctcaacctgg     480
gaactgcagt ggaaactgga cgactagagt gtggtagagg gtagcggaat tcctggtgta     540
gcagtgaaat gcgtagagat caggaggaac atccatggcg aaggcagcta cctggaccaa     600
gactgacact gaggcacgaa agcgtgggga gcaaacagga ttagataccc tggtagtcca     660
cgccctaaac gatgcgaact ggatgttggg tgcaatttgg cacgcagtat cgaagctaac     720
gcgttaagtt cgccgcctgg ggagtacggt cgcaagactg aaactcaaag gaattgacgg     780
```

```
gggcccgcac aagcggtgga gtatgtggta taattcgatg caacgcgaag aaccrtacct    840
ggccrtgaca tctcgagaac tttccagaga tggattggtg ccttcgggaa ctcgaacaca    900
ggtgctgcat ggctgtcgtc agctcgtgtc gtgagatgtt gggttaagtc ccgcaacgag    960
cgcaacccct gtccttagtt gccagcacgt aatggtggga actctaagga gaccgccggt   1020
gacaaaccgg aggaaggtgg ggatgacgtc aagacatcat ggcccttacg ccagggcta    1080 cacacgtact acaatggtag ggacagaggg ctgcaagccg cgacggtaa gccaatccca    1140 gaaaccctat ctcagtccgg attggagtct gcaactcgac tccatgaagt cggaatcgct   1200
agtaatcgca gatcagcatt gctgcggtga atacgttccc gggccttgta cacaccgccc   1260
gtcacaccat gggagttt                                                  1278

<210> SEQ ID NO 2
<211> LENGTH: 467
<212> TYPE: DNA
<213> ORGANISM: Stenotrophomonas maltophilia
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (454)..(455)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (464)..(465)
<223> OTHER INFORMATION: n is a, c, g, or t

<400> SEQUENCE: 2
tgcagtcgaa cggcagcaca ggagagcttg ctctctgggt ggcgagtggc ggacgggtga     60
ggaatacatc ggaatctact ttttcgtggg ggataacgta gggaaactta cgctaatacc    120
gcatacgacc tacgggtgaa agcaggggat cttcggacct tgcgcgattg aatgagccga    180
tgtcggatta gctagttggc ggggtaaagg cccaccaagg cgacgatccg tagctggtct    240
gagaggatga tcagccacac tggaactgag acacggtcca gactcctacg ggaggcagca    300
```

```
gtggggaata ttggacaatg ggcgcaagcc tgatccagcc ataccgcgtg ggtgaagaag      360
gccttcgggt tgtaaagccc ttttgttggg aaanaaancc agcnggttaa nacccggttg      420
ggangacggt acccnaagaa taagcaccnn cnannttcan gccnnca                    467
```

<210> SEQ ID NO 3
<211> LENGTH: 481
<212> TYPE: DNA
<213> ORGANISM: Stenotrophomonas maltophilia
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t

<400> SEQUENCE: 3

```
cgtcntcccn accgggtatt aaccagctgg atttctttcc caacaaaagg gctttacaac       60
ccgaaggcct tcttcaccca cgcggtatgg ctggatcagg cttgcgccca ttgtccaata      120
ttccccactg ctgcctcccg taggagtctg gaccgtgtct cagttccagt gtggctgatc      180
atcctctcag accagctacg gatcgtcgcc ttggtgggcc tttaccccgc caactagcta      240
atccgacatc ggctcattca atcgcgcaag gtccgaagat ccoctgcttt cacccgtagg      300 tcgtatgcgg tattagcgta agtttcccta cgttatcccc cacgaaaaag tagattccga      360
tgtattcctc acccgtccgc cactcgccac ccagagagca agctctcctg tgctgccgtt      420
cgacttgcan gtgttaggcc taccgccagc gttcactctn anccaggatc aanctctcca      480
a                                                                     481
```

<210> SEQ ID NO 4
<211> LENGTH: 227
<212> TYPE: DNA
<213> ORGANISM: Stenotrophomonas maltophilia
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:

```
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (199)..(203)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (210)..(215)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (224)..(225)
<223> OTHER INFORMATION: n is a, c, g, or t

<400> SEQUENCE: 4
nacncnngca gtcgaacggc agcacaggan agcttgctct ctgggtggcg agtggcggnc      60
gggtgaggaa tacatcggaa tctactttt cgtgggggat aacgtaggga aacttacgct     120
aataccgcat acgacctacg ggtgaaagca ggggatcttc ggaccttgcg cgantgaatg     180
agccnatgtc ggantancnn nnnggngggn nnnnngncca ccanngc                  227

<210> SEQ ID NO 5
<211> LENGTH: 488
<212> TYPE: DNA
<213> ORGANISM: Stenotrophomonas maltophilia
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
```

<400> SEQUENCE: 5

```
tnnggnngtc ntcccnaccg ggtattaacc agctggattt ctttcccaac aaaagggctt    60
tacaacccga aggccttctt cacccacgcg gtatggctgg atcaggcttg cgcccattgt   120
ccaatattcc ccactgctgc ctcccgtagg agtctggacc gtgtctcagt tccagtgtgg   180
ctgatcatcc tctcagacca gctacggatc gtcgccttgg tgggccttta ccccgccaac   240
tagctaatcc gacatcggct cattcaatcg cgcaaggtcc gaagatcccc tgctttcacc   300
cgtaggtcgt atgcggtatt agcgtaagtt tccctacgtt atccccacg aaaaagtaga    360 ttccgatgta ttcctcaccc gtccgccact cgccacccag agagcaagct ctcctgtgct   420
gccgttcgac ttgcatgtgt taggcctacc gccagcgttc actctgagcn aggatcaaac   480 tctccaan                                                            488
```

<210> SEQ ID NO 6
<211> LENGTH: 487
<212> TYPE: DNA
<213> ORGANISM: Stenotrophomonas maltophilia
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (461)..(462)
<223> OTHER INFORMATION: n is a, c, g, or t
<220> FEATURE:
<221> NAME/KEY: misc_feature
<222> LOCATION: (469)..(471)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (482)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t

<400> SEQUENCE: 6

```
ncntgcagtc gncggcagca caggagagct tgctctctgg gtggcgagtg gcggacgggt    60
gaggaataca tcggaatcta cttttttcgtg ggggataacg tagggaaact tacgctaata  120
ccgcatacga cctacgggtg aaagcagggg atcttcggac cttgcgcgat tgaatgagcc   180
gatgtcggat tagctagttg gcggggtaaa ggcccaccaa ggcgacgatc cgtagctggt   240
ctgagaggat gatcagccac actggaactg agacacggtc cagactccta cgggaggcag   300
cagtggggaa tattggacaa tgggcgcaag cctgatccag ccataccgcg tgggtgaaga   360
aggccttcgg gttgtaaagc cctttttgttg ggaaagaaat ccagctggtt aatacccggt   420
tgggatgacg gtacccaaag aataagcacc ggctaacttc nngccagcnn ncggtaatan   480 anttnt                                                              487
```

<210> SEQ ID NO 7
<211> LENGTH: 478
<212> TYPE: DNA
<213> ORGANISM: Stenotrophomonas maltophilia
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (463)..(464)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t

<400> SEQUENCE: 7
tcntcccnac cgggtattaa ccagctggan ttctttccca acaaaagggc tttacaaccc      60
gaaggccttc ttcacccacg cggtatggct ggatcaggct tgcgcccatt gtccaatatt     120
ccccactgct gcctcccgta ggagtctgga ccgtgtctca gttccagtgt ggctgatcat     180
cctctcagac cagctacgga tcgtcgcctt ggtgggcctt taccccgcca actagctaat     240
ccgacatcgg ctcattcaat cgcgcaaggt ccgaagatcc cctgctttca cccgtaggtc     300
gtatgcggta ttagcgtaag tttccctacg ttatccccca cgaaaaagta gattccgatg     360
tattcctcac ccgtccgcca ctcgccaccc agagagcaag ctctcctgtg ctgccgttcg     420
acttgcatgt gttaggccta ccgccagcgt tcactctnan ccnngancaa actctccn      478

<210> SEQ ID NO 8
<211> LENGTH: 477
<212> TYPE: DNA
<213> ORGANISM: Stenotrophomonas maltophilia
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (469)..(471)
<223> OTHER INFORMATION: n is a, c, g, or t

<400> SEQUENCE: 8

```
cntgcnagtc gaacggcagc acaggagagc ttgctctctg ggtggcgagt ggcggacggg    60
tgaggaatac atcggaatct acttttttcgt gggggataac gtagggaaac ttacgctaat   120
accgcatacg acctacgggt gaaagcaggg gatcttcgga ccttgcgcga ttgaatgagc   180
cgatgtcgga ttagctagtt ggcggggtaa aggcccacca aggcgacgat ccgtagctgg   240
tctgagagga tgatcagcca cactggaact gagacacggt ccagactcct acggggaggca   300 gcagtgggga atattggaca atgggcgcaa gcctgatcca gccataccgc gtgggtgaag   360
aaggccttcg ggttgtaaag cccttttgtt gggaagaaaa tccagctggt taatacccgg   420
ttgggatgac ggtacccaaa gaataagcac cggctaactt cngccagcnn nggtaat      477
```

<210> SEQ ID NO 9
<211> LENGTH: 481
<212> TYPE: DNA
<213> ORGANISM: Stenotrophomonas maltophilia
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (459)..(461)
<223> OTHER INFORMATION: n is a, c, g, or t
<220> FEATURE:
<221> NAME/KEY: misc_feature
<222> LOCATION: (463)..(464)
<223> OTHER INFORMATION: n is a, c, g, or t
<220> FEATURE:
<221> NAME/KEY: misc_feature
<222> LOCATION: (469)..(470)
<223> OTHER INFORMATION: n is a, c, g, or t

<400> SEQUENCE: 9

```
gtcntcccna ccgggtatta accagctgga tttctttccc aacaaagggg ctttacaacc    60
cgaaggcctt cttcacccac gcggtatggc tggatcaggc ttgcgcccat tgtccaatat   120
tccccactgc tgcctcccgt aggagtctgg accgtgtctc agttccagtg tggctgatca   180
tcctctcaga ccagctacgg atcgtcgcct tggtgggcct ttaccccgcc aactagctaa   240
tccgacatcg gctcattcaa tcgcgcaagg tccgaagatc ccctgctttc acccgtaggt   300
cgtatgcggt attagcgtaa gtttccctac gttatccccc acgaaaaagt agattccgat   360
gtattcctca cccgtccgcc actcgccacc cagagagcaa gctctcctgt gctgccgttc   420
gacttgcatg tgttaggcct accgccagcg ttcactctnn ncnngatcnn actctccaaa   480
a                                                                    481
```

<210> SEQ ID NO 10
<211> LENGTH: 482
<212> TYPE: DNA
<213> ORGANISM: Stenotrophomonas maltophilia
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (459)..(461)
<223> OTHER INFORMATION: n is a, c, g, or t
<220> FEATURE:
<221> NAME/KEY: misc_feature
<222> LOCATION: (465)..(465)

<223> OTHER INFORMATION: n is a, c, g, or t
<220> FEATURE:
<221> NAME/KEY: misc_feature
<222> LOCATION: (467)..(469)
<223> OTHER INFORMATION: n is a, c, g, or t
<220> FEATURE:
<221> NAME/KEY: misc_feature
<222> LOCATION: (473)..(475)
<223> OTHER INFORMATION: n is a, c, g, or t
<220> FEATURE:
<221> NAME/KEY: misc_feature
<222> LOCATION: (481)..(482)
<223> OTHER INFORMATION: n is a, c, g, or t

<400> SEQUENCE: 10

| | | | | | |
|---|---|---|---|---|---|
| nntgcagtcg | aacggcagca | caggagagct | tgctctctgg | gtggcgagtg | gcggacgggt | 60 |
| gaggaataca | tcggaatcta | cttttttcgtg | ggggataacg | tagggaaact | tacgctaata | 120 |
| ccgcatacga | cctacgggtg | aaagcagggg | atcttcggac | cttgcgcgat | tgaatgagcc | 180 |
| gatgtcggat | tagctagttg | gcggggtaaa | ggcccaccaa | ggcgacgatc | cgtagctggt | 240 |
| ctgagaggat | gatcagccac | actggaactg | agacacggtc | cagactccta | cgggaggcag | 300 |
| cagtggggaa | tattggacaa | tgggcgcaag | cctgatccag | ccataccgcg | tgggtgaaga | 360 |
| aggccttcgg | gttgtaaagc | ccttttgttt | ggaaagaaat | ccagctggtt | aatacccggt | 420 |
| tgggatgacg | gtacccaaag | aataagcacc | ggctaactnn | ntgcnannng | ccnnngtaat | 480 |
| nn | | | | | | 482 |

<210> SEQ ID NO 11
<211> LENGTH: 1280
<212> TYPE: DNA
<213> ORGANISM: Stenotrophomonas maltophilia

<400> SEQUENCE: 11

| | | | | | |
|---|---|---|---|---|---|
| gggataacgt | agggaaactt | acgctaatac | cgcatacgac | ctacgggtga | aagcagggga | 60 |
| tctacggacc | ttgcgcgatt | gaatgagccg | atgtcggatt | agctagttgg | cggggtaaag | 120 |
| gcccaccaag | gcgacgatcc | gtagctggtc | tgagaggatg | atcagccaca | ctggaactga | 180 |
| gacacggtcc | agactcctac | gggagccagc | agtggggaat | attggacaat | gggcgcaagc | 240 |
| ctgatccagc | ataccgcgt | gggtgaagaa | ggccttcggg | ttgtaaagcc | ttttcttgg | 300 |
| gaaagaaatc | cagctggtta | atacccggtt | gggatgacgg | tacccaaaga | ataagcaccg | 360 |
| gctaacttcg | tgccagcagc | cgcggtaata | cgaagggtgc | aagcgttact | cggaattact | 420 |
| gggcgtaaag | cgtgcgtagg | tggttgttta | agtctgttgt | gaaagccctg | ggctcaacct | 480 |
| gggaactgca | gtggaaactg | gacgactaga | gtgtggtaga | gggtagcgga | attcctggtg | 540 |
| tagcagtgaa | atgcgtagag | atcaggagga | acatccatgg | cgaaggcagc | tacctggacc | 600 |
| aagactgaca | ctgaggcacg | aaagcgtggg | gagcaaacag | gattagatac | cctggtagtc | 660 |
| cacgccctaa | acgatgcgaa | ctggatgttg | ggtgcaattt | ggcacgcagt | atcgaagcta | 720 |
| acgcgttaag | ttcgccgcct | ggggagtacg | gtcgcaagac | tgaaactcaa | aggaattgac | 780 |
| gggggcccgc | acaagcggtg | gagtatgtgg | tataattcga | tgcaacgcga | agaaccttac | 840 |
| ctggccttga | catctcgaga | actttccaga | gatggattgg | tgccttcggg | aactcgaaca | 900 |
| caggtgctgc | atggctgtcg | tcagctcgtg | tcgtgagatg | ttgggttaag | tcccgcaacg | 960 |
| agcgcaaccc | ttgtccttag | ttgccagcac | gtaatggtgg | gaactctaag | gagaccgccg | 1020 |
| gtgacaaacc | ggaggaaggt | ggggatgacg | tcaagcatc | atggccctta | cggccagggc | 1080 |
| tacacacgta | ctacaatggt | agggacagag | ggctgcaagc | cggcgacggt | aagccaatcc | 1140 |

```
cagaaaccct atctcagtcc ggattggagt ctgcaactcg actccatgaa gtcggaatcg    1200
ctagtaatcg cagatcagca ttgctgcggt gaatacgttc ccgggccttg tacacaccgc    1260
ccgtcacacc atgggagttt                                                1280

<210> SEQ ID NO 12
<211> LENGTH: 20
<212> TYPE: DNA
<213> ORGANISM: Stenotrophomonas maltophilia

<400> SEQUENCE: 12
agagtttgat cctggctcag                                                  20

<210> SEQ ID NO 13
<211> LENGTH: 19
<212> TYPE: DNA
<213> ORGANISM: Stenotrophomonas maltophilia

<400> SEQUENCE: 13
ggttaccttg ttacgactt                                                   19
```

METHODS FOR PRODUCING SEMICONDUCTOR NANOPARTICLES

CROSS REFERENCE TO RELATED APPLICATIONS

This application claims priority as a US National stage filing under 35 U.S.C. §371 based on PCT/US2012/051068, filed Feb. 17, 2014, which in turn claims the benefit of U.S. Provisional Application No. 61/524,126 filed Aug. 16, 2011, each of which are incorporated herein by reference.

BACKGROUND OF THE INVENTION

Semiconductor crystals, including semiconductor nanoparticles such as quantum dots, are useful to provide imaging and lighting in many technological applications. For example, semiconductor quantum dots (hereinalso "QDs") have been used as biocompatible probes for in vivo imaging and medical diagnostics, as potential replacements or enhancers to LED lighting, as modifiers or replacements in LED display technology, as active materials in photovoltaic cells (so-called quantum dot solar cells), and as potential catalysts for water splitting (i.e., hydrogen generation) for fuel cell applications, as well as in semiconductors, biomedical diagnostics, imaging, targeting and drug delivery, biosensors, lighting, display technology, solar cells, and photovoltaics, for example.

A major barrier to the utilization of quantum dots in commercial applications is the high cost associated with conventional chemical synthesis due to high temperatures, pressures and toxic solvents, thereby requiring specialized, expensive waste disposal procedures. Furthermore, multi-stage synthesis methods are necessary to 'cap' chemically-synthesized QDs in order to enhance water solubility. Therefore, more cost-efficient and environment friendly methods of producing and using soluble quantum dots, as well as less toxic quantum dot compositions, are desirable.

SUMMARY OF THE INVENTION

New and desirable semiconductor nanoparticle technologies, including novel methods, systems, and compositions, are provided herein. In one embodiment, provided are bacterial-based synthesis methods for producing semiconductor nanoparticles that do not require expensive reagents, solvents or other materials. The methods produce large quantities of soluble QDs from a continuous biological process at a cost less than $30/g, thereby enabling the producing of semiconductor nanoparticles such as QDs on a scale necessary for their ready use in a number of otherwise cost-prohibitive commercial applications.

In one embodiment, the technology involves a method of manufacturing quantum dots using live bacteria, preferably in a continuous process, wherein the process provides quantum dots having preselected properties. In an example, provided is a method of making semiconductor nanoparticles, the method involving the steps of providing a selected bacterial organism that is tolerant to a selected metal salt; placing the selected bacterial organism in an aqueous environment comprising at least the selected metal salt; and leaving the bacterial organism in the aqueous solution for a period of time sufficient to utilize the metal salt to assemble semiconductor nanoparticles, and harvesting the semiconductor nanoparticles without requiring lysis of the bacterial organism.

In another example, provide is a method of making semiconductor nanoparticles, the method involving the steps of providing a selected bacterial organism; placing the selected bacterial organism in an aqueous environment comprising at least one metal salt; and leaving the bacterial organism in the aqueous solution for a period of time sufficient to ingest the metal salt and to assemble semiconductor nanoparticles, and harvesting the nanoparticles without requiring lysis of the bacterial organism, wherein the nanoparticles have an average particle size of between about 1 nm to about 10 nm.

In still another example, provided is a method of making semiconductor crystals, the method involving the steps of providing a selected bacterial organism; placing the selected bacterial organism in an aqueous environment comprising at least one metal salt comprising cadmium; and leaving the bacterial organism in the aqueous solution for a period of time sufficient to ingest the metal salt and to assemble semiconductor nanoparticles, and harvesting the nanoparticles wherein the semiconductor nanoparticles comprise semiconductor crystals that are soluble in water In another embodiment, the technology involves a water soluble semiconductor nanoparticle made by a bacterial organism.

Other embodiments will be apparent from the description provided herein, and from the claims and drawings submitted herewith.

BRIEF DESCRIPTION OF THE DRAWINGS

The present invention will hereinafter be described in conjunction with the appended drawing figures wherein like numerals denote like elements.

FIGS. 12-21 illustrate genotyping results comprising sequence listings for exemplary bacterial organisms of the species *S. maltophilia* useful in accordance with the present invention.

DETAILED DESCRIPTION OF THE PREFERRED EMBODIMENTS

Figures 1A, 1B:
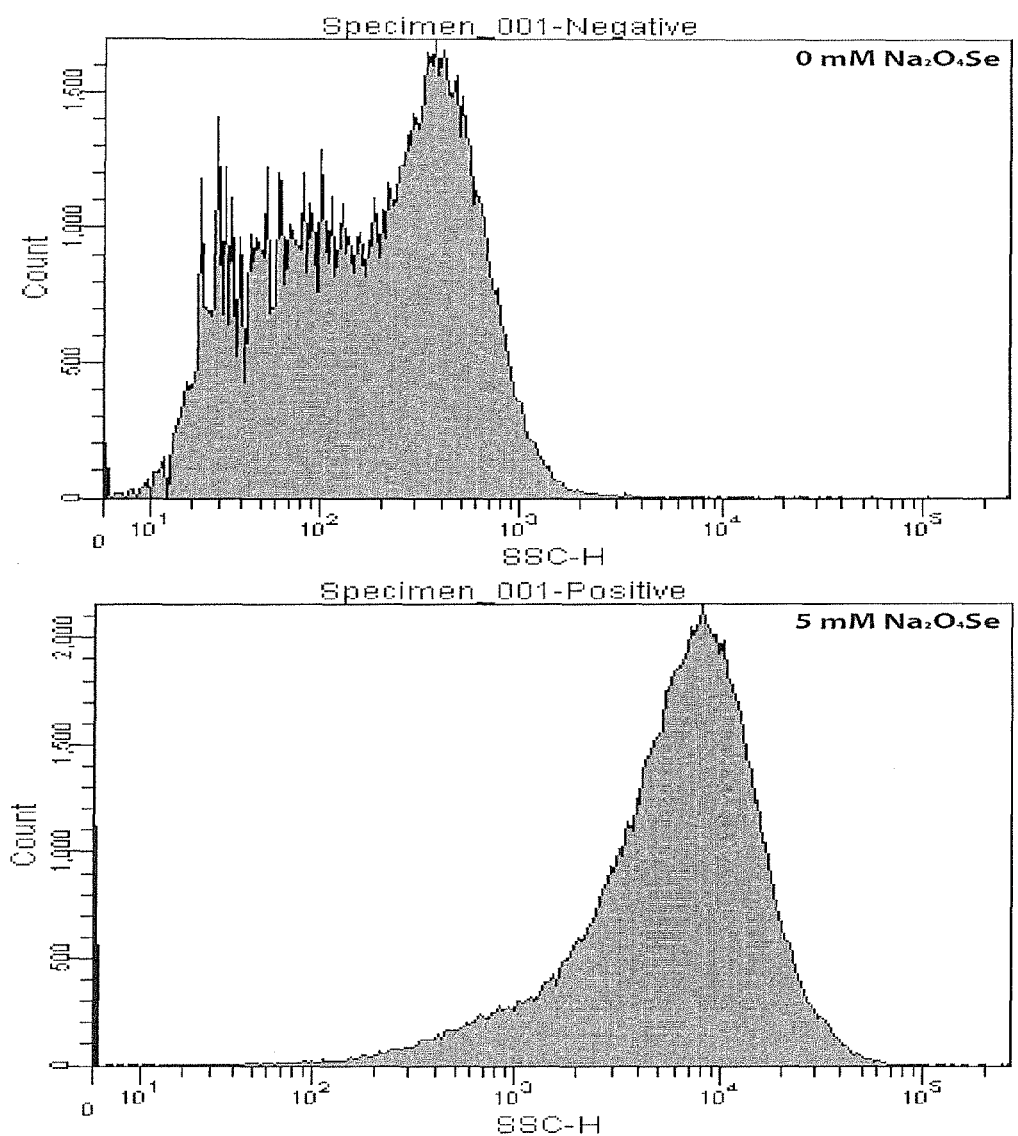
FIGS. 1a-1b are graphs illustrating results from side-scatter intensity (SSC) measured from *S. maltophilia* cell suspensions treated with 5 mM sodium selenite, in accordance with an embodiment of the present invention.

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. It being understood that various changes may be made in the function and arrangement of elements without departing from the spirit and scope of the invention, as set forth in the appended claims.

To aid in describing the invention, definitions and terms are used in the specification and claims to describe portions of the present invention. These definitions are merely intended to assist in describing and claiming the invention and are not intended to limit the invention in any way. In addition, reference numerals that are introduced in the specification in association with a drawing figure may be repeated in one or more subsequent figures without additional description in the specification in order to provide context for other features.

Quantum dots are the established technology to provide imaging and lighting in many technological applications. For example, semiconductor quantum dots have been used as biocompatible probes for in vivo imaging and medical diagnostics, as potential replacements or enhancers to LED lighting, as modifiers or replacements in LED display technology, as active materials in photovoltaic cells (so-called quantum dot solar cells), and as potential catalysts for water splitting (i.e., hydrogen generation for fuel cell applications). A major barrier to the utilization of quantum dots (QDs) in commercial applications is the high cost associated with conventional chemical synthesis, which necessitates high temperatures, pressures and toxic solvents to produce and solubilize QDs, thereby requiring specialized, expensive waste disposal procedures. Moreover, there is no known method of biologically and controllably producing semiconductor nanocrystals, such as quantum dots, having a controlled particle size and uniform particle size distribution, using biological organisms, and certainly none that are compatible with continuous production by live organisms in a continuous process. Therefore, more cost-efficient and environment friendly methods, including biological methods, of producing and using soluble quantum dots, as well as less toxic quantum dot compositions, are desirable.

Desirable semiconductor nanoparticle technologies, including novel methods, systems, and compositions, are provided herein. Robust, reproducible production of large amounts of semiconductor QDs from bacterial cultures during continuous growth has been conceived and reduced to practice, without a need for extensive post growth processing or modification. The result is novel, water soluble semiconductor nanoparticles active and useful for numerous commercial applications in lighting, display, imaging, diagnostics, photovoltaics or hydrogen generation.

In one embodiment, provided are bacterial-based synthesis methods for producing crystalline semiconductor nanoparticles such as quantum dots. Those methods use aqueous, environmentally friendly media and methods, and do not require expensive reagents, solvents or other materials. Nonetheless, the inventive methods are capable of producing large (g/L) quantities of QDs from a continuous process at a cost less than $30/g, thereby enabling the continuous producing of QDs on a scale necessary for their successful use in a number of otherwise cost-prohibitive commercial applications. The inventive activities herein combine the diverse but complementary skills of inventors from two fields. Mr. Berger is an expert in protein and microbial engineering, while Mr. McIntosh is an expert in structure-function relationships of functional solid materials and electrocatalysis. These skills combined to conceive and create unique methodologies and environmentally benign, in situ semiconductor nanoparticle biosynthesis from live organisms such as gram-negative bacteria.

The present invention describes the facile synthesis and purification of large quantities of semiconductor nanoparticles from aqueous solutions through direct fermentation using a bacteria that is one of the phylum Proteobacteria. Preferably, the bacteria is also one of the class of Gammaproteobacteria. More preferably, the bacteria is also one of the order of Xanthomonadales. More preferably, the bacteria is also one of the family Xanthomonadaceae. More preferably, the bacteria is also one of the genus: *Stenotrophomonas*. More preferably, the bacteria is also one of the species *Stenotrophomonas* (*S.*) *acidaminiphila, S. dokdonensis, S. koreensis, S. maltophilia, S. nitritireducens,* and *S. rhizophila*. By way of further example, genus of bacteria that are compatible with the present invention are those of the genus *Frateuria, Luteimonas, Lysobacter, Nevskia, Pseudoxanthomonas, Rhodanobacter, Stenotrophomonas* (already listed above), *Xanthomonas,* and *Xanthomonas*. By way of further example, bacteria that are compatible further include: Order: Pseudomonadales, Family: Pseudomonadaceae, Genus: *Pseudomonas,* and Species: *Pseudomonas (P.) aeruginosa* group, such as: *Pseudomonas (P.) aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea, P. chlororaphis* group, *P. agarici, P. asplenii, P. aurantiaca, P. aureofaciens, P. chlororaphis, P. corrugate, P. fragi, P. lundensis, P. taetrolens, P. fluorescens, P. antarctica, P. azotoformans, 'P. blatchfordae', P. brassicacearum, P. brenneri, P. cedrina, P. corrugate, P. fluorescens, P. gessardii, P. libanensis, P. mandelii, P. marginalis, P. mediterranea, P. meridian, P. migulae, P. mucidolens, P. orientalis, P. panacis, P. proteolytica, P. rhodesiae, P. synxantha, P. thivervalensis, P. tolaasii, P. veronii, P. pertucinogena* group, *P. denitrificans, P. pertucinogena, P. putida* group, *P. cremoricolorata, P. fulva, P. monteilii, P. mosselii, P. oryzihabitans, P. parafulva, P. plecoglossicida, P. putida, P. stutzeri* group, *P. balearica, P. luteola, P. stutzeri, P. syringae* group, *P. amygdale, P. avellanae, P. caricapapayae, P. cichorii, P. coronafaciens, P. ficuserectae, 'P. helianthi', P. meliae, P. savastanoi, P. syringae, 'P. tomato', P. viridiflava, P. incertae sedis, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophila, P. psychrotolerans, P. rathonis, P. reptilivora, P. resiniphila, P. rhizosphaerae, P. rubescens, P. salomonii, P. segitis, P. septic, P. simiae, P. suis, P. thermotolerans, P. toyotomiensis, P.*

*tremae, P. trivialis, P. turbinellae, P. tuticorinensis, P. umsongensis, P. vancouverensis, P. vranovensis, P. xanthomarina.*

Most preferably, the organism is one of *Stenotrophomonas maltophilia*. *S. maltophilia* has been shown by the inventors to generate novel nanoparticles of relevant materials that are believed to be unable to be synthesized by conventional chemical (non-biological) methods, and having unique properties such as high water solubility that are believed to result from the solubilizing/capping agent used by the selected bacteria. The inventors continue to investigate the inventive materials and methods herein, including all chemical and physical attributes of the resulting QD particles from biosynthesis as described herein.

Cadmium Sulfide (CdS) and Cadmium Selenide (CdSe) are narrow band gap semiconductors with suitable conduction band potentials to effectively catalyze this reaction. There exists a continuing and unmet need in this field to develop more stable nanostructured photocatalysts, by creating solid solutions of CdS and/or CdSe with more stable materials or utilizing other material sets. One common barrier to new photocatalyst development is the ability to synthesize nanoparticle-based materials with controlled size and composition. This requires a robust, flexible and scalable synthesis technique. This is especially true of CdS and CdSe nanoparticles, which are used in quantum dot or other semiconductor nanoparticle applications; for both nanomaterials, state-of-the art synthesis (prior to the present invention) requires elevated temperatures (>200 degrees C.) and pressures with coordinating solvents such as octadecene and trioctylphosphine that are volatile, highly corrosive, and environmentally hazardous. The combination of high temperatures and pressures with corrosive solvent mixtures are essential in previously known synthetic methods for controlling the rate of nanoparticle synthesis and subsequent size distribution, but ultimately limit the flexibility and scalability of the process due to high costs associated with solvent consumption and waste disposal.

The present invention avoids the toxicity and cost of known methods to produce semiconductor nanoparticles. A new, exciting alternative to the traditional chemical synthesis route of semiconductor nanoparticles such as nanodisperse CdSe particles is the application of in situ, biosynthesis from bacteria. The present inventive approach has several advantages for developing a robust, scalable and flexible production method, as described herein: 1) Synthesis can be performed under ambient temperatures and pressures; 2) it requires only aqueous growth media rather than coordinating solvents; 3) it allows for control of particle synthesis through external (growth media, temperature) or internal (directed evolution) manipulation of the bacterial system; and 4) is amenable to high-throughput selection and screening techniques to alter nanomaterial properties.

As further described herein, the inventors have selected as an initial example *Stenotrophomonas maltophilia*, a gram-negative, facultatively aerobic bacteria, as an environmentally-benign system for scalable synthesis of novel Se, CdS and CdSe nanomaterials. One of the remarkable properties of *S. maltophilia* is its high resistance to a wide range of heavy metals (at concentrations exceeding 10 mM in aqueous solution), including cadmium, selenium, cobalt, gold, silver and lead (Chien at al., 2007; Pages et al., 2008). Investigations into the structure of metal precipitates formed from environmental *S. maltophilia* isolates reveal a wide diversity of nanostructured materials, encompassing 'mesh'-like networks of elemental selenium nanowires and spherical nanoparticle precipitates (ranging from 20-200 nm) of selenium and cadmium sulfate (Dungan et al., 2003; Pages et al., 2008; Yadav et al., 2008). Most importantly, many of the observed nanostructures are unique in the sense that they are inaccessible using traditional inorganic chemical synthesis methods. Thus, the combination of robust growth at ambient conditions in the presence of high metal concentrations and ability to synthesize novel nanostructured Se, CdS and CdSe nanomaterials make it an ideal system for nanoparticle synthesis.

In an example, *S. maltophilia* is an obligate gram-negative, aerobic bacteria that is found ubiquitously throughout the environment. The inventors have isolated and identified a strain of *S. maltophilia* that is capable of aerobic growth in the presence of high concentrations of cadmium (>1 mM) in aqueous solution. The strain was initially identified and characterized as having the sequence listing of table 1, which shows genotyping of environmental *S. maltophilia* isolate, wherein individual colonies of *S. maltophilia* were selectively isolated from environmental (soil) samples using previously described methods using imipenem and DL-methionine (Bullet et al., 1995). The strains were identified using colony PCR for specific gene products and confirmed using 16S PCR sequencing with 'universal' primers as described previously for bacterial identification (DOI 10.1128/JCM.01228-07). Importantly, the inventors have confirmed that the processes herein cause the bacteria to genetically evolve, thereby creating new sub-strains that may have different sequence listings. It is impracticable, if not impossible, to predict every genetic modification that will be incurred for this strain, as well as for its sub-strains, and the same is true for the other bacteria identified herein as being compatible with the inventive quantum dot methods and products described herein. Nonetheless, the teachings herein are sufficient to enable one skilled in the art to successfully practice the invention after a reasonable degree of experimentation, regardless of the bacteria selected among those listed herein.

Through selection of the bacteria, and subsequent control of varying growth conditions and times, the bacteria transform aqueous cadmium acetate and/or cadmium chloride solutions into monodisperse, 1-4 nm CdS semiconductor nanocrystals (a type of QD). For example, by growing strain LU8 in the presence of increasing concentrations of cadmium acetate, LU8 was adapted to tolerate (i.e., grow aerobically) in the presence of elevated levels of aqueous cadmium (>1 mM), and through an iterative growth and selection procedure in the presence of 1 mM cadmium acetate, specific strains capable of producing extracellular, luminescent CdS QDs were isolated based on observed luminescence present in culture. Additional characterization (absorbance spectroscopy, electron microscopy) are detailed in subsequent sections.

These biologically-synthesized CdS QDs can be harvested directly from culture supernatant by simple centrifugation to remove cells, and exhibit identical spectral properties to commercially available CdS QDs produced through conventional chemical synthesis. Importantly, it is not necessary to lyse the bacteria to obtain the QDs, since the QDs are excreted by the bacteria, and can be recovered from the media leaving the bacteria to thrive and continue to ingest cadmium, biologically assemble QDs, and excrete the QDs. No other technology is known that approximates such a continuous, biological-based manufacturing process for QDs.

TABLE 1

Sequence listing for a preferred exemplary strain of *S. maltophilia* identified as "LU08"

GGGATAACGTAGGGAAACTTACGCTAATACCGCATACGACCTACGGGTGAAAGCAGGGGATCTACGGA

CCTTGCGCGATTGAATGAGCCGATGTCGGATTAGCTAGTTGGCGGGGTAAAGGCCCACCAAGGCGACGA

TCCGTAGCTGGTCTGAGAGGATGATCAGCCACACTGGAACTGAGACACGGTCCAGACTCCTACGGGAGC

CAGCAGTGGGGAATATTGGACAATGGGCGCAAGCCTGATCCAGCCATACCGCGTGGGTGAAGAAGGCC

TTCGGGTTGTAAAGCCCTTTTCTTGGGAAAGAAATCCAGCTGGTTAATACCCGGTTGGGATGACGGTACC

CAAAGAATAAGCACCGGCTAACTTCGTGCCAGCAGCCGCGGTAATACGAAGGGTGCAAGCGTTACTCGG

AATTACTGGGCGTAAAGCGTGCGTAGGTGGTTGTTTAAGTCTGTTGTGAAAGCCCTGGGCTCAACCTGG

GAACTGCAGTGGAAACTGGACGACTAGAGTGTGGTAGAGGGTAGCGGAATTCCTGGTGTAGCAGTGAA

ATGCGTAGAGATCAGGAGGAACATCCATGGCGAAGGCAGCTACCTGGACCAAGACTGACACTGAGGCA

CGAAAGCGTGGGGAGCAAACAGGATTAGATACCCTGGTAGTCCACGCCCTAAACGATGCGAACTGGAT

GTTGGGTGCAATTTGGCACGCAGTATCGAAGCTAACGCGTTAAGTTCGCCGCCTGGGGAGTACGGTCGC

AAGACTGAAACTCAAAGGAATTGACGGGGGCCCGCACAAGCGGTGGAGTATGTGGTATAATTCGATGC

AACGCGAAGAACCTTACCTGGCCTTGACATCTCGAGAACTTTCCAGAGATGGATTGGTGCCTTCGGGAAC

TCGAACACAGGTGCTGCATGGCTGTCGTCAGCTCGTGTCGTGAGATGTTGGGTTAAGTCCCGCAACGAG

CGCAACCCTIGTCCTTAGTTGCCAGCACGTAATGGTGGGAACTCTAAGGAGACCGCCGGTGACAAACCG

GAGGAAGGTGGGGATGACGTCAAGACATCATGGCCCTTACGGCCAGGGCTACACACGTACTACAATGGT

AGGGACAGAGGGCTGCAAGCCGGCGACGGTAAGCCAATCCCAGAAACCCTATCTCAGTCCGGATTGGA

GTCTGCAACTCGACTCCATGAAGTCGGAATCGCTAGTAATCGCAGATCAGCATTGCTGCGGTGAATACGT

TCCCGGGCCTTGTACACACCGCCCGTCACACCATGGGAGTTT

Selection of other bacteria. A common feature of the bacteria used in the present methods is that they ingest a metal salt comprising at least one metal that is useful in forming a semiconductor. For example, metals useful in forming semiconductors include, but are not limited to, the group of I-VI, II-VI, IV-VI and III-V semiconductors as listed in the periodic table of the elements and known to those skilled in the art. By way of further non-limiting example, cadmium is useful as such a metal. By way of still further non-limiting example, cadmium from cadmium sulfide (group II-VI) and cadmium from cadmium selenide (group II-VI) is compatible with formation of a semiconductor. In any case, the bacteria selected is tolerant to such metal salts, and either is, or quickly becomes, tolerant when exposed to high concentrations of the selected metal and metal salt As used herein, "tolerant" means a colony of bacteria grow (i.e., cells undergo division to increase the total number of cells in culture over time) in an aqueous solution of the target metal salt (such as cadmium acetate, for example) at a concentration greater than 1 mM. "Moderately tolerant" as used herein means that the bacteria survive and grow (i.e., cells undergo division to increase the total number of cells in culture over time) at a concentration of the metal salt of greater than 1 mM and up to 5 mM. The term "Highly Tolerant" or "hyper-tolerant" as used herein means the bacteria survive and grow (i.e., cells undergo division to increase the total number of cells in culture over time) at a concentration of the metal salt of greater than 5 mM.

In experimentation by others, such as Chien et al. (Chien et al., 2007), Bai et al. (Bai et al., 2009a; Bai et al., 2009b) and Pages et al. (Pages et al., 2008), other bacteria, including *Rhodopseudomonas*, *Rhodobacter* and *Stenotromophonas*, have survived at high concentrations of cadmium, making them possibly capable of QD synthesis (Chien et al., 2007). However, in that experimentation observing high tolerance of *Stenotrophomonas* to cadmium (Chien et al., 2007), synthesis of nanocrystalline materials (i.e., QDs) has not been proven. For example, in the case of a laboratory strain of *Stenotrophomonas*, electron microscopy was used to observe CdS deposits in cell culture (Pages et al., 2008). However, no spectroscopic characterization effort was reported to determine whether the deposits luminesce (which is one exemplary characteristic of a QD). Furthermore, the deposits were heterogeneous in terms of size (i.e., many different apparent sizes in a broad mixture of deposits within a batch).

Further, while there are reported examples of observed luminescence from cell cultures using other types of bacteria (such as *E. coli* and not *Stenotrophomonas*) upon addition of cadmium, however, there is no experimental proof that the luminescence involves QDs (Mi et al., 2011). Furthermore, the inventors are not aware of any prior art publications teaching or suggesting any methods involving extracellular QDs, nor of any size control over QDs demonstrated. Indeed, the lack of any size variation in any publication suggests that any reported luminescence in research by others was not in fact QDs, rather simply aggregates of cadmium-containing materials.

There is a suggestion in 2 publications by Sweeney et al. (Sweeney et al., 2004) and Kang et al. (Kang et al., 2008) indicating that CdS QDs can be produced from cell extracts derived from an engineered *E. coli* strain. However, that proposed process requires transformation of cells with a specific plasmid, cell growth, lysis, addition of exogenous substrates, and subsequent synthesis in vitro (i.e., from cell lysates) under highly-controlled conditions. That is vastly different from the inventive methods herein, which involve continuously growing cultures of bacteria, and thus continuous production of QDs. Further, the *E. coli* methods constitute a complicated, multiple-stage process that leads to an uncontrolled, broad size distribution of any aggregates or QDs, as opposed to the tightly controlled size of QDs by the inventive methods herein using bacteria from another unrelated phylum, genus, class and species, as more fully described later herein.

Thus, some advantageous, unprecedented, and novel features of the instant methods are:

(1) Synthesis of QDs from continuously growing cells in aerobic culture. For example, we add cadmium to a culture of organisms and observe growth in the resulting aerobically growing culture (e.g., in shake flasks or biological reactors, for example).

(2) Precise control over QD size. The methods herein allow for control over QD size, such as by controlling growth rate of the organisms to control particle size of the QDs they produce.

(3) Demonstration that product is indeed QDs incorporating CdS. As opposed to EM images from other research groups that are low-resolution and at much larger length scales and merely show aggregates, our EM images are at least near-scale and permit us to conclude to a scientific certainty that the product of our methods includes CdS QDs. Moreover, our methods and data show that our CdS QDs are of a controlled, substantially homogeneous particle size distribution, which is unprecedented by any other research group known to the inventors.

(4) Simplicity in recovery and purification, and a continuous process. Unlike many biologically manufactured products, that require large amounts of processing steps, including cell lysis, to process samples and extract product from culture, thereby making the processes non-continuous (aka "batch manufacturing"). In contrast, the QDs we synthesize are produced extracellularly, and therefore can be collected directly from culture without needing to lyse, extract or otherwise process cells prior to synthesis or recovery. The present inventive methods are amenable to continuous manufacture and processing to harvest QDs.

In short, no prior art publication is known to the inventors that teaches or suggests (1) proven extracellular biological synthesis of QDs; (2) continuous production in aerobically growing culture; (3) control over QD size through varying growth rate; and (4) uniform and controllable QD size distribution.

Without being limited by theory, the inventors suspect that, the reason the inventive methods can control QD size and growth is because the exemplary bacteria selected are tolerant to Cd, but are not hypertolerant. In other words, hypertolerant strains could cause bulk CdS precipitation (aggregates, not QDs), whereas tolerant strains produce nanoparticles of QD that are precipitated in the extracellular environment (i.e., QDs).

Furthermore, the inventors note that the particular steps of our methods are inventive, and yield the following unique features and advantages: (1) continuous, extracellular QD production in aerobic growth culture; (2) precise control of particle size through varying growth rate or time (i.e., tailorable, scalable process for a desired and specific wavelength/size of CdS QD); (3) simple, straightforward purification (e.g. without a need for cell lysis, fractionation or addition of exogenous components—just the media formulation and cadmium, and the cells growing aerobically in culture synthesize, secrete and solubilze QDs of a given size).

In an example, the methods herein include methods for selecting and growing a bacteria that produces Quantum Dots, comprising the steps of:

1. Isolating individual colonies of a given Phylum (or genus, species, sub-species) of organism, such as on non-selective Luria broth (LB)- or other nutrient rich agar plates.

2. Selecting acceptable colonies and cultivate them, such as in non-selective liquid LB or other nutrient rich liquid media for 12-16 hours at 37 degrees C. under aerobic conditions, such as in a shake flask culture at 200-223 rpm.

3. Centrifuging the culture at low speed (2,000 g) and decant spent media.

4. Re-suspending cells in M9 minimal medium containing an initial concentration of 0.1 mM cadmium acetate, cadmium chloride or other aqueous cadmium salt, as well as 1 mM L-cysteine.

5. Growing the cells, such as for about 12-24 hours in M9+L-cys+cadmium medium at about 37 degrees C. under aerobic conditions, such as in a shake flask culture at 200-223 rpm.

6. Plating the cells, such as on agar plates containing M9 media with equivalent concentration of cadmium as was in solution (i.e., 0.1 mM initially).

7. Isolating individual colonies, followed by cultivating, such as in M9 minimal media+L-cys containing twice the previous amount of cadmium (i.e., for an initial concentration of 0.1 mM cadmium acetate, increase to 0.2 mM cadmium acetate) for 24 hours at 37 degrees C. under aerobic conditions, such as in a shake flask culture at 200-225 rpm.

8. Assessing the presence of CdS QDs, such as by using exemplary methods involving:

a. Absorbance spectroscopy of culture supernatant—centrifuge cultures at low speed to remove cells, collect culture supernatant, and measure UV-visible absorbance spectrum. Determine maximal wavelength for QDs suspended in culture supernatant.

b. Direct observation of cultures under UV illumination—directly image cultures under UV lamp and observe spontaneous luminescence. Note color of apparent luminescence from culture.

9. Repeating steps 6-9 until appropriate absorbance spectrum and spontaneous luminescence is observed (Step 8).

10. Once a set of conditions is determined (Step 8) that satisfy a given criterion (QD luminescence and absorbance at a specific wavelength of interest), harvest the cell strain and preserve it for future production (such as by storing at −80 degrees C. in glycerol-LB storage medium) for long term preservation and future use is a manufacturing organism.

A significant use and purpose of the present invention is to produce semiconductor quantum dots from aqueous solutions in large quantity at a cost-effective scale, which would enable their use in a wide range of commercial technologies. While there has been great interest in using QDs for solar cells, lighting and display technologies, and hydrogen production, the prohibitively high costs associated with chemical synthesis has prevented their large-scale use in commercial applications. Our method is capable of producing QDs on a commercial (g/L) scale limited by raw material (i.e., metal) rather than process (i.e., synthesis) costs, thereby enabling their use in a wide variety of commercial applications.

In an example, the invention utilizes a strain of *S. maltophilia* (designated herein as LU8, and further described in Table 1) isolated from soil on the Lehigh University campus, Bethlehem, Pa. This bacteria has been shown by the inventors to exhibit growth in the presence of high cadmium concentrations, and to convert aqueous metal salts to semiconductor nanoparticles having an average size of between about 1 to about 4 nanometers.

Reference will now be made to the attached drawings, which further describe and enable the invention. FIGS. 1a-1b are graphs illustrating results from side-scatter intensity (SSC) measured from S. maltophilia cell suspensions treated with 5 mM sodium selenite, in accordance with an embodiment of the present invention. Measurements represent an average population of $10^6$ cells.

Figure 2:
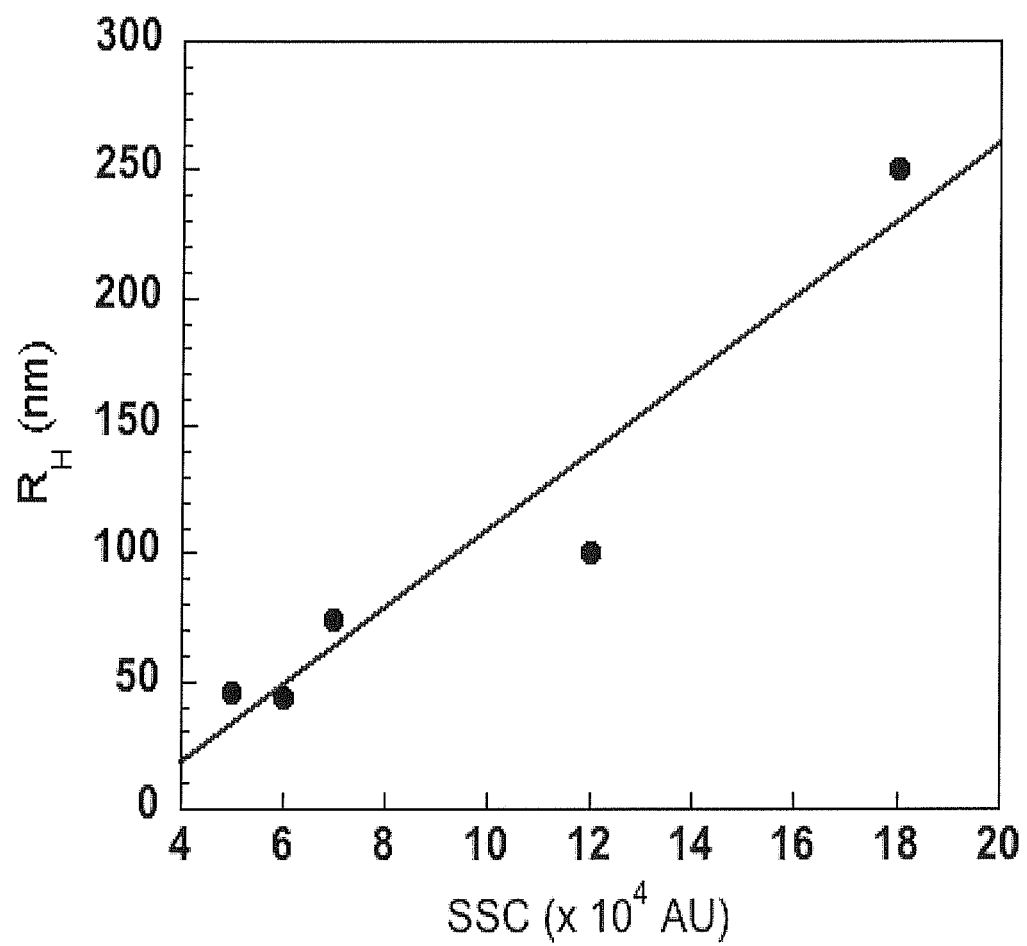
FIG. 2 is another graph illustrating side-scatter intensity (SSC) measured from *S. maltophilia* cell suspensions treated with 5 mM sodium selenite, correlating mean particle size of extracellularly produced nanoparticles measured from purified cell extracts in accordance with an embodiment of the present invention.

FIG. 2 is another graph illustrating side-scatter intensity (SSC) measured from S. maltophilia cell suspensions treated with 5 mM sodium selenite, correlating mean particle size of extracellularly produced nanoparticles measured from purified cell extracts in accordance with an embodiment of the present invention. Measurements represent samples isolated from an average population of $10^6$ cells.

Figure 3:
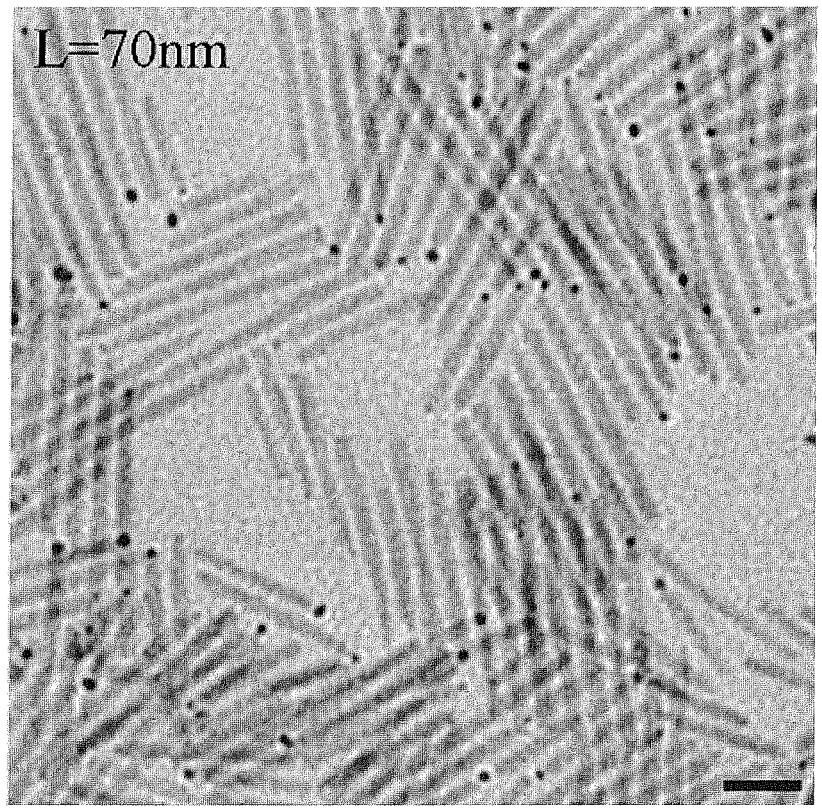
FIG. 3 is a photograph illustrating CdSe/CdS hetero nanorods topped with Pt nanoparticles in accordance with an embodiment of the present invention.

FIG. 3 is a photograph illustrating CdSe/CdS hetero nanorods topped with Pt nanoparticles in accordance with an embodiment of the present invention.

Figure 4:
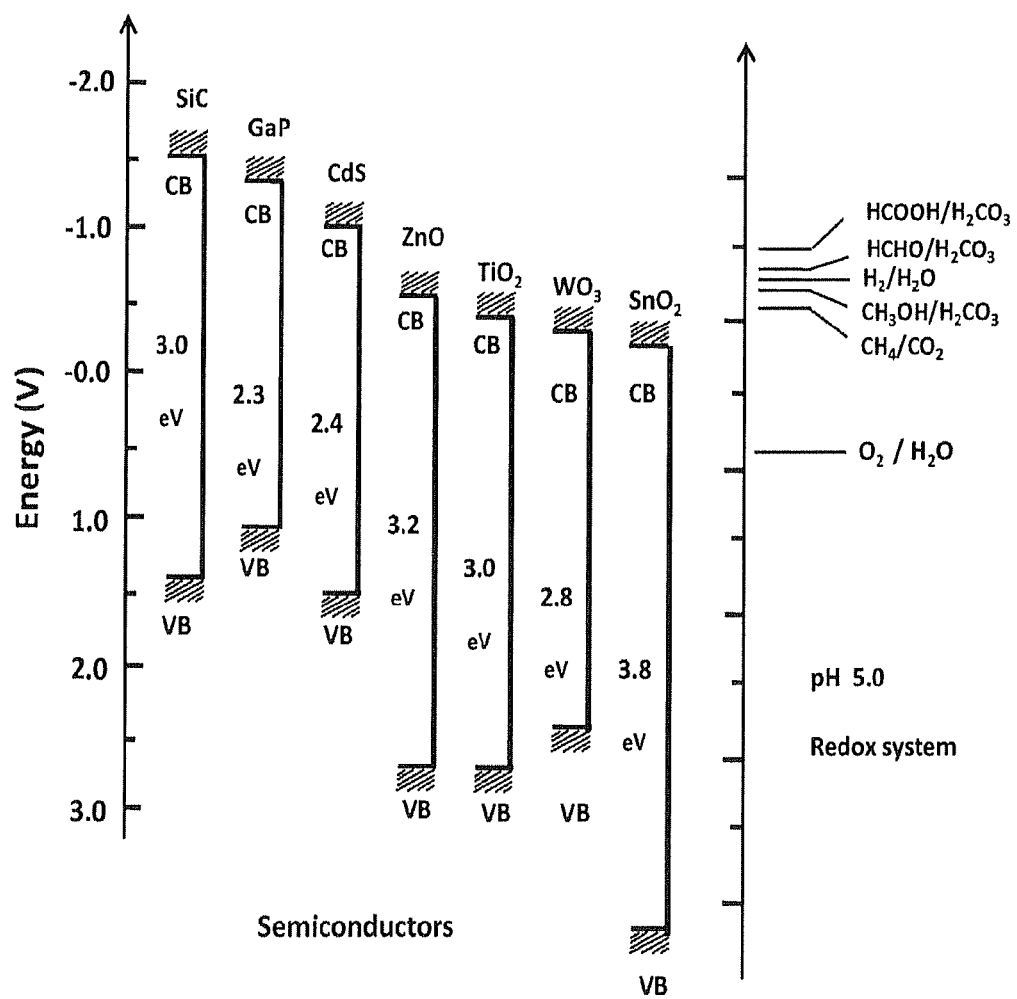
FIG. 4 is a chart illustrating band gaps and positions of some desirable QD materials relative to desired reaction potentials in accordance with an embodiment of the present invention.

FIG. 4 is a chart illustrating band gaps and positions of some desirable QD materials relative to desired reaction potentials in accordance with an embodiment of the present invention.

Figure 5:
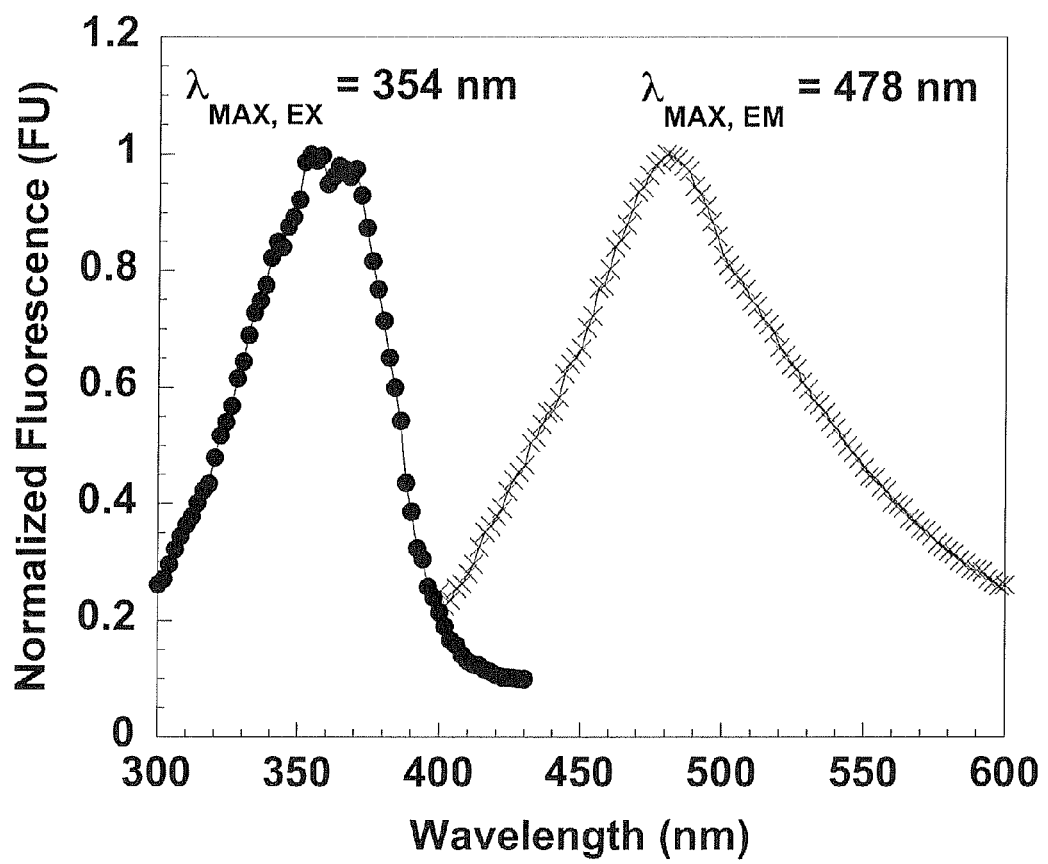
FIG. 5 is a chart illustrating photoluminescence spectra for purified, 1.8 nm CdS QDs in accordance with an embodiment of the present invention.

FIG. 5 is a chart illustrating photoluminescence spectra for purified, 1.8 nm CdS QDs. The 1MAX for excitation and emission are consistent with previously reported values for 2 nm CdS QDs. Based on absorbance spectra and using rhodamine 6G as a reference, we estimate a quantum yield for 2 nm QDs of near 50%. Absorbance (blue, peak at 354 nm) and emission (yellow, peak at 478 nm) spectra for a ~1.8 nm CdS quantum dot. Absorbance occurs at a shorter wavelength (higher energy) that emission.

Figure 6:
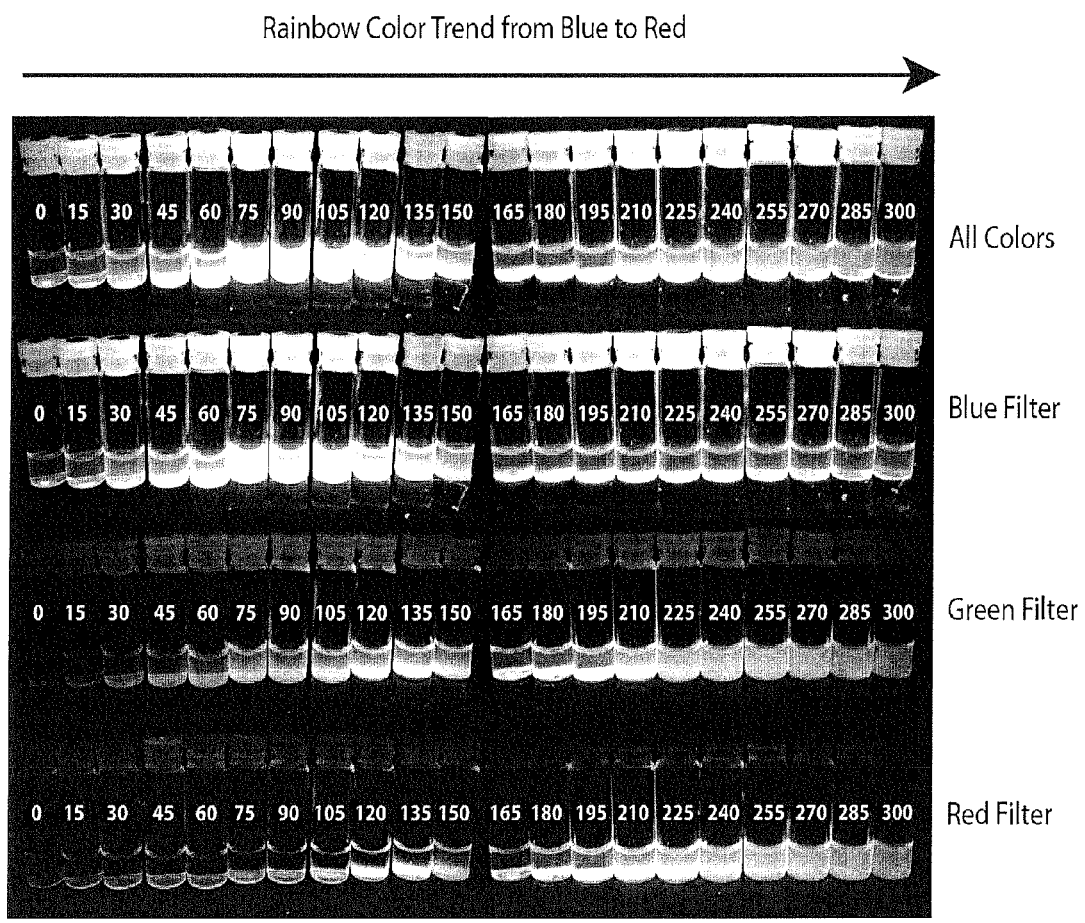
FIG. 6 is a photograph illustrating visible fluorescence of CdS QDs in accordance with an embodiment of the present invention.

FIG. 6 is a photograph illustrating visible fluorescence of CdS QDs in accordance with an embodiment of the present invention. Visible fluorescence of CdS quantum dots under ultra-violet light illumination. The numbers are the particle growth time in minutes. The observed change in color from blue to red is indicative of an increase in particle size from short to long growth times. The larger particles have smaller band gap energy, leading to emission of lower energy light. The top image is a black and white conversion of the full color images. The three images beneath this are filtered for blue, green, and red light respectively, highlighting the blue, green, and red colors of the particles.

Figure 7:
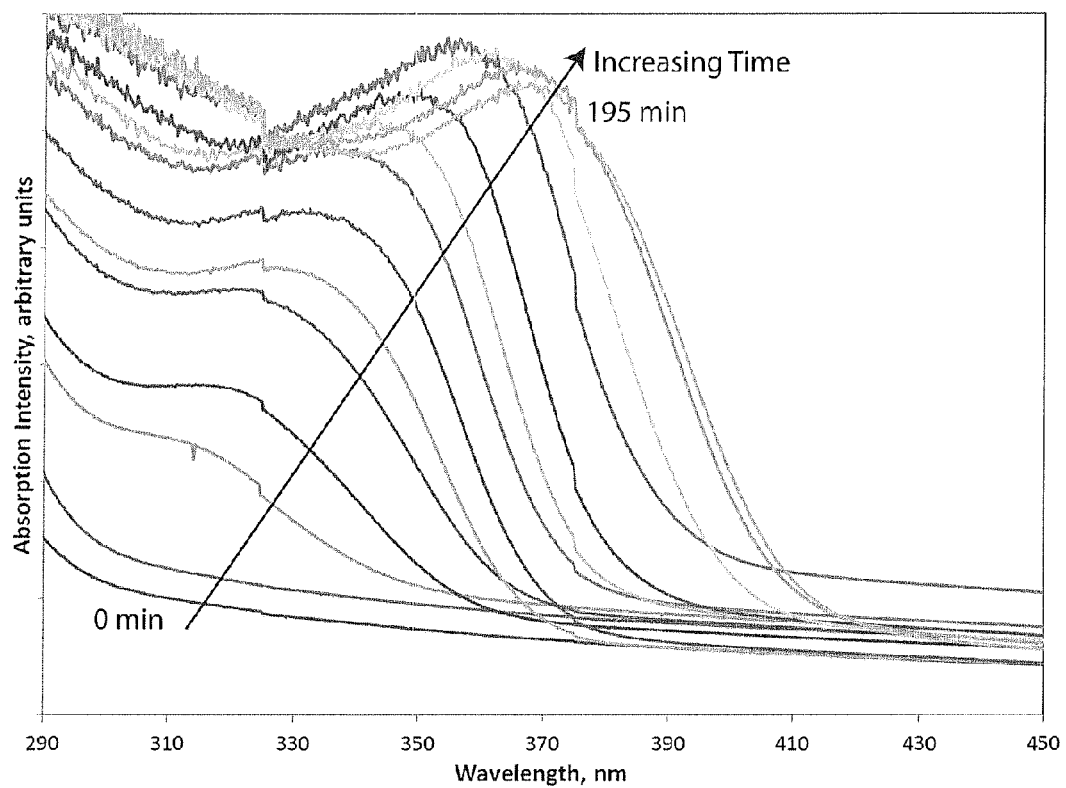
FIG. 7 is a graph illustrating ultraviolet-visible light absorbance spectra of the nanoparticle suspensions shown in FIG. 6 in accordance with the present invention.

FIG. 7 is a graph illustrating ultraviolet-visible light absorbance spectra of the nanoparticle suspensions shown in FIG. 6. Each line along the direction of the arrow is a unique spectra, which were measured in 15 minute intervals. The figure shows an increase in absorption wavelength and intensity from 30-195 minutes of growth time, corresponding to an increase in particle size. No adsorption is seen prior to 30 minutes.

Figure 8:
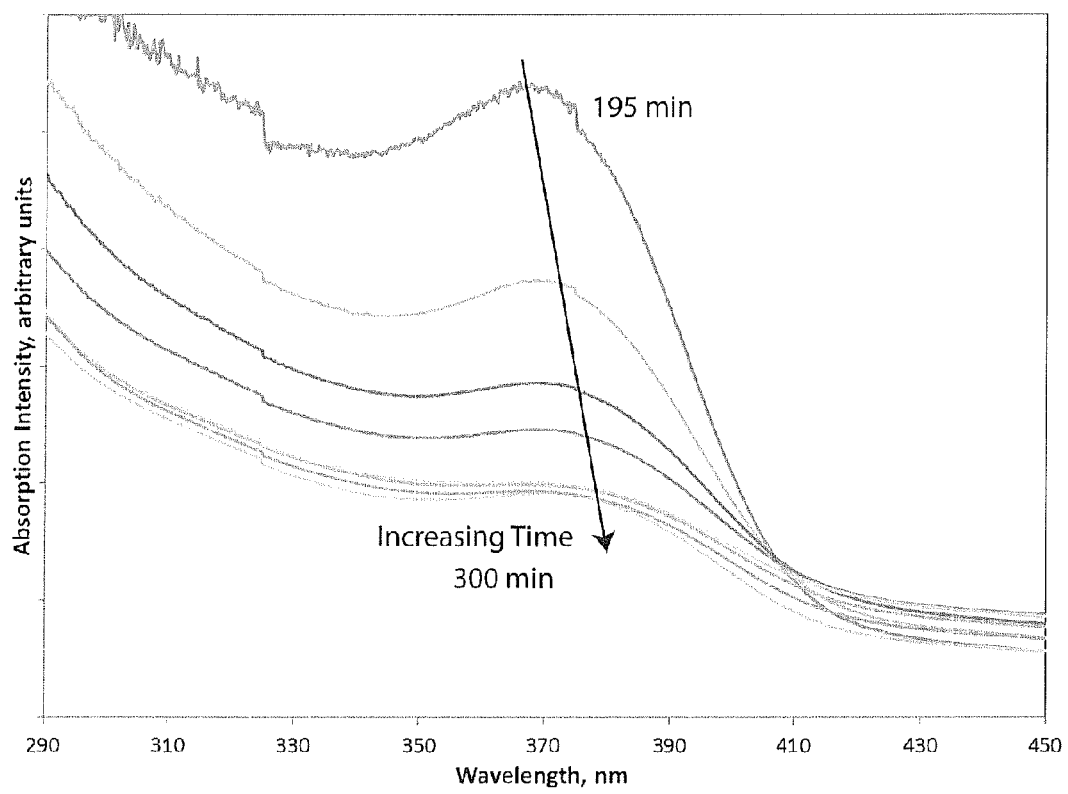
FIG. 8 is another graph illustrating ultraviolet-visible light absorbance spectra of the nanoparticle suspensions shown in FIG. 6.

FIG. 8 is a graph illustrating ultraviolet-visible light absorbance spectra of the nanoparticle suspensions shown in FIG. 6. Each line along the direction of the arrow is a unique spectra, which were measured in 15 minute intervals. The figure shows an increasing absorption wavelength from 195-255 minutes, corresponding to an increase in particle size, with a decrease in intensity corresponding to fewer suspended particles. No change is observed between 255 and 300 minutes.

Figure 9:
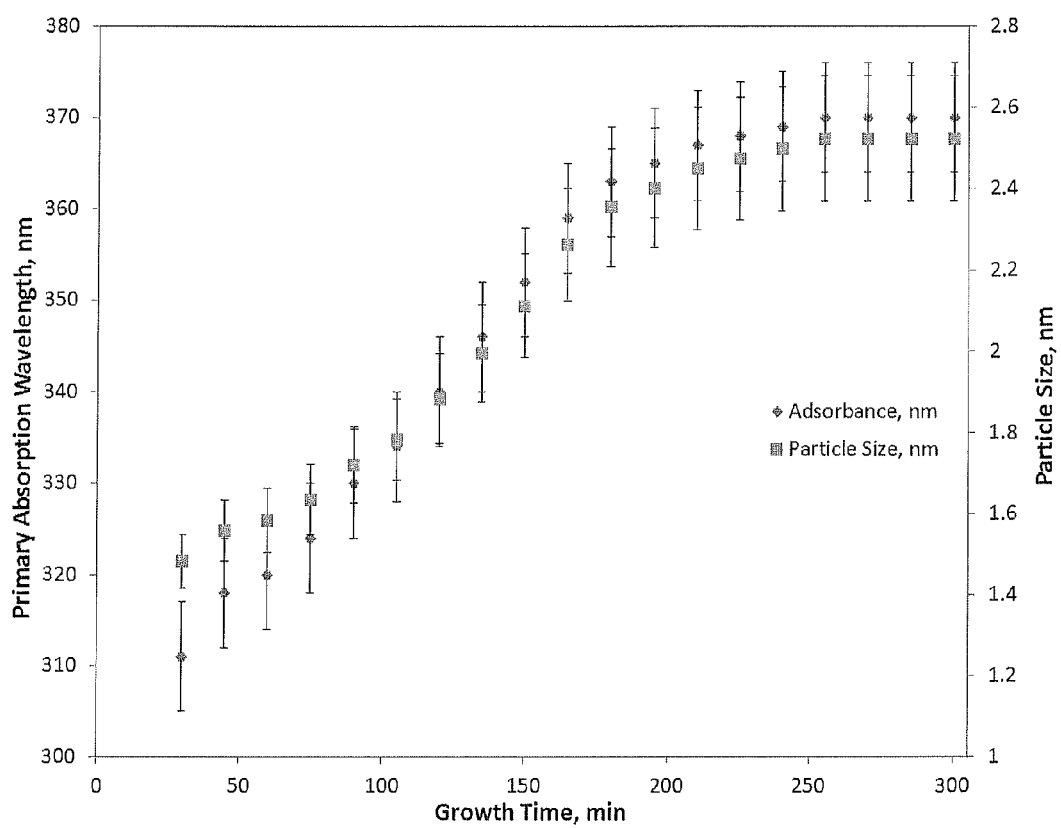
FIG. 9 is a graph illustrating absorption wavelength versus growth time and corresponding particle size in accordance with the present invention.

FIG. 9 is a graph illustrating absorption intensity versus wavelength as a function of growth time for the bacterially-produced QDs illustrated in FIG. 6 in accordance with an embodiment of the present invention. The corresponding calculated QD sizes are shown for each time point.

Figure 10:
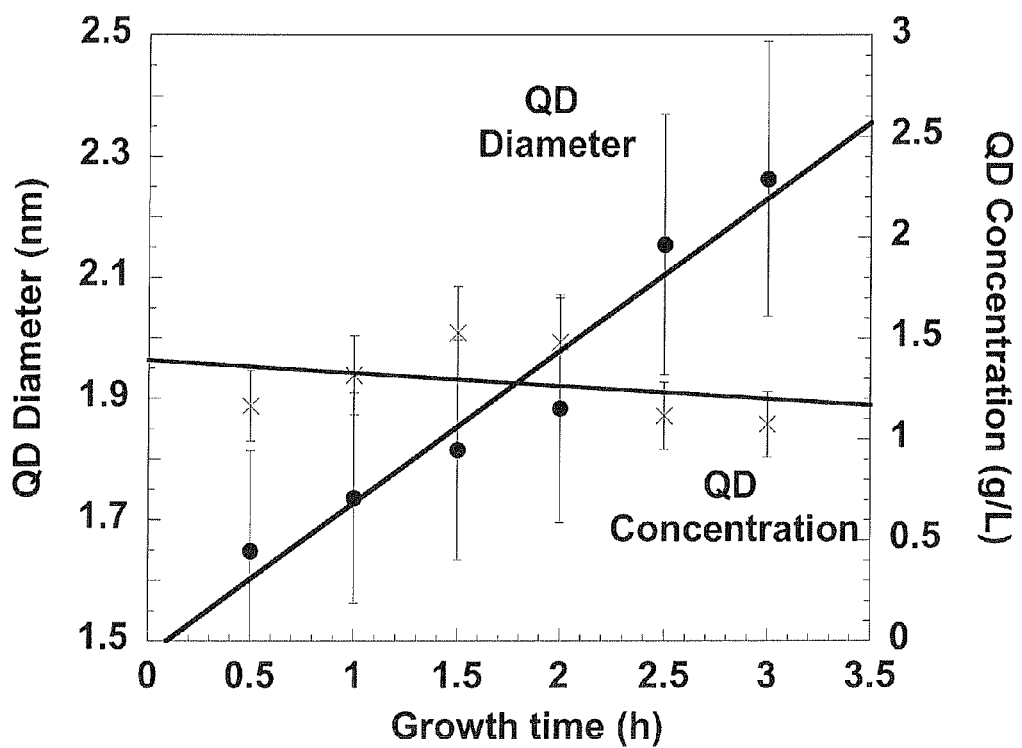
FIG. 10 is a chart illustrating CdS QD diameter and concentration in culture as a function of bacteria growth time for a strain of *S. maltophilia* identified herein as strain LU08 in accordance with an embodiment of the present invention.

FIG. 10 is a chart illustrating CdS QD diameter and concentration in culture as a function of bacteria growth time for a strain of S. maltophilia identified herein as strain LU08 in accordance with an embodiment of the present invention. Apparent CdS QD diameter and concentration in culture as a function of LU08 growth time. Diameter and concentration are estimated from absorbance spectra based on previously described equations specific to CdS QDs. Trendlines are a guide to the eye. Error bars are based on reported standard errors used in estimation of diameter and concentration.

Figure 11:
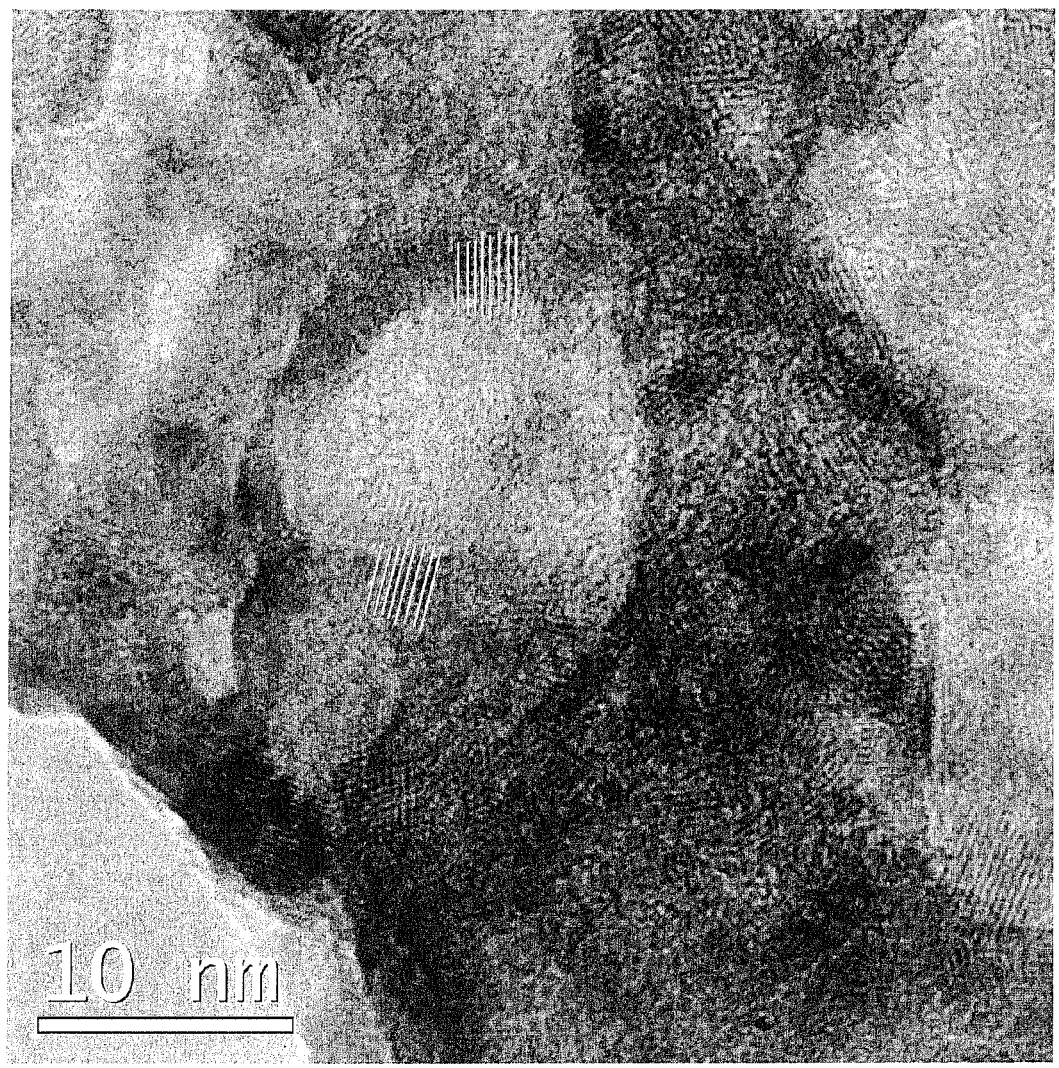
FIG. 11 is an SEM image illustrating nano-sized QDs made in accordance with an embodiment of the present invention.

FIG. 11 is a photograph illustrating nano-sized QDs made in accordance with an embodiment of the present invention.

FIG. 12-21 include sequence listings for exemplary bacterial organisms of the species S. maltophilia in accordance with useful in the present invention.

By way of further example, attached as FIGS. 5-11, illustrate the absorbance and fluorescence spectra of purified exemplary nanoparticles produced by the inventive methods herein by the inventors. The nanoparticles were shown to exhibit identical properties to purified, commercially available QDs made using conventional chemical synthesis, and also correspond to numerous published chemical synthesis protocols as well as to images of purified QDs illuminated using UV light (Baskoutas and Terzis, 2006; Bera et al., 2010; Boatman et al., 2005; Neeleshwar et al., 2005; Pal et al., 2002; Yu et al., 2003). The inventors have further personally observed the orange-yellow color of the CdS nanoparticles biologically synthesized, which color is indicative of QDs having an average particle size of between 1 nm to 3 nm.

In addition to QDs, the present inventive methods are compatible with manufacture of other nanostructures including rods, spheres, and cubes (as shown in FIG. 3), as well as to other semiconductor materials, metals, metal oxides, metal sulfides, metal phosphates. Such other structures and compositions can have application in catalysis, electronics, and optics. Furthermore, the inventors reasonably expect that engineering of bacterial strains will incorporate thiolated peptides or polymers, in addition to the exemplary L-cysteine example described herein. Furthermore, functionalization of particles from culture (such as direct functionalization) will provide additional means to diversify the spectral properties, solubility, stability and self-assembly of the particles as novel materials.

ILLUSTRATIVE EXAMPLES

Example 1

Preparation of Reagents. Luri broth (LB) agar and broth are recommended for isolation and cultivation of Stenotrophomonas maltophilia species. LB agar and broth are based on standard formulations described previously for microbial growth (Green and Sambrook, 2012). To generate LB broth into 1 L of distilled water: 10 g tryptone, 5 g yeast extract, 10 g NaCl. To generate LB agar, the formulation for LB broth is used, with the addition of 15 g of agar per L broth. These materials are readily available from commercial supplies such as Alfa Aesar. Storage media is recommended for long-term storage and preservation of the evolved or otherwise identified organism. In the case of Stenotrophomonas maltophilia, storage media can be based on standard formulations used previously for long-term microbial storage (Green and Sambrook, 2012). To generate storage media, prepare LB media as described above, and add 10% glycerol. These materials are readily available from commercial supplies such as Alfa Aesar.QD synthesis broth is recommended for production of QDs from cell culture. To generate 800 mL of 5×M9 salts in distilled water: 64 g $Na_2HPO_4$-$7H_2O$, 15 g $KH_2PO_4$, 2.5 g NaCl, 5.0 g $NH_4Cl$. To generate 50 mL of L-cysteine stock solution in distilled water, add 2 g L-cysteine. To generate 100 mL cadmium acetate stock solution in distilled water, add 2.3 g of cadmium acetate. To generate QD broth into 1 L of distilled water: 200 mL of 5×M9 salts, 0.03 mL of 1 M $MgSO_4$ in distilled water, 1 g of $NH_4Cl$, 1-3 mL of L-cysteine stock solution, and 10 mL of cadmium acetate stock solution. These materials are readily available from commercial supplies such as Alfa Aesar.

Example 2

QD Synthesis Protocol 100 mL of LB broth was autoclaved for 20 minutes at 121° C. After the 100 mL broth had cooled to room temperature, it was inoculated with 0.2 mL of *Stenotrophomonas maltophilia* strain LU8 that had been stored at −80° C. in storage media, and incubated for 12-18 h at 37° C. in an orbital shaker at 200-225 rpm. After 12-16 h incubation, the optical density measured at 600 nm ($OD_{600}$) LU8 reached ~1.0-9.0.

The 100 mL LB cultures were centrifuged at low speed (3,000-9,000 RPM), and the spent LB media decanted. The cell mass was resuspended in 100 mL of fresh QD broth. Prior to use, QD broth was autoclaved for 20 minutes at 121° C., allowed to cool to room temperature and 0-4 g of sugar (glucose, trehalose or mannose) per L broth added aseptically. The resuspended cell mass was transferred aseptically to QD broth, thereby diluting the cell suspension to an OD600 0.4-0.8, and the diluted cell suspension incubated for 0.2-4.0 h at 37° C. in an orbital shaker at 200-225 rpm.

Example 3

QD Harvesting Protocol

At a given growth time, 100 mL cultures were removed from the orbital shaker, centrifuged at low speed (3,000-9,000 RPM), and the supernatant removed from the sedimented cell mass. 1 L of distilled water is pre-chilled to 4 C in a 1 L glass flask with added stir bar, and placed on a magnetic stir plate. 10 mL aliquots of supernatant were transferred to a dialysis bag (3,500 MWCO), placed in the pre-chilled, distilled water and dialyzed for 8-12 h with continuous stirring (100-200 rpm). The distilled water was exchanged at least once and the dialysis procedure performed at least twice.

After dialysis, 10 mL samples are collected from the dialysis bag and stored for at least 12 h at −80° C. Frozen 10-50 mL samples are then transferred to a lyophilizer, and solvent removed from QDs by evaporation. Typical operating pressures for the lyophilizer are 0.01-0.001 bar, and operating times are 12-24 h. Solids containing purified QDs are removed from the lyophilizer and stored at −80° C.

Example 4

QD Size and Concentration

Purified solids (Example 3) resuspended in distilled water or culture supernatants (Example 1 and Example 2) containing QDs were characterized using ultraviolet (UV)-visible absorbance spectroscopy. QDs are semiconductor nanocrystals that exhibit unique optical properties due to a combination of their band gap energy and quantum confinement effect (Baskoutas and Terzis, 2006; Bera et al., 2010). Specifically, the size of the QD dictates its ability to emit light at a specific wavelength due to quantum confinement effects, and the band gap energy of a given QD is inversely proportional to its size (and hence emission wavelength). Thus the absorbance spectrum of a given QD solution provides information on its size, band gap energy and concentration.

FIG. 5 is a fluorescence excitation and emission spectra from culture supernatants harvested at 150 minutes. The measured excitation maximum and emission maximum are consistent with expected values for a 1.8 nm CdS QD (Yu et al., 2003). FIG. 6 illustrates spontaneous luminescence from cultures illuminated under ultraviolet (UV) light as a function of culture growth time, demonstrating QD nanocrystal production from culture and control over QD size and corresponding control of absorption, fluorescence and luminescence properties. This provides direct evidence to support control of the range of band gap energies (FIG. 4).

FIGS. 7 and 8 illustrates absorbance spectra collected from culture supernatants in 15-minute intervals as well as images of spontaneous luminescence from culture supernatants illuminated under UV light. Note the shape and wavelength maximum of the absorbance spectra and corresponding color of the QD solution are consistent with previously published spectra for CdS QDs prepared using various chemical synthesis methods (Baskoutas and Terzis, 2006; Bera et al., 2010; Boatman et al., 2005; Neeleshwar et al., 2005; Pal et al., 2002; Yu et al., 2003).

Previous work in the art has described absorbance properties of QDs, including extinction coefficients, which can be used to determine QD size and concentration in solution (Yu et al., 2003). Using UV-visible absorbance spectroscopy, the inventors measured the absorbance maximum and calculated an effective particle size and concentration as a function of growth time. The results of these calculations are illustrated in FIG. 9. Over the range of LU8 growth times (0 to 4 hours, by way of non-limiting example), QDs were produced at an effective concentration of approximately 1 g/L in culture over a range of sizes, from about 1 to about 3 nm in average particle size, over time. FIG. 10 illustrates a subsequent experiment, which was used to assess the change in apparent particle size and quantum dot concentration as a function of bacterial growth time via the measured primary absorption wavelength. Thus, particle size can be controlled through controlling growth time, and particle concentration remains constant as a function of growth time.

FIG. 11 is a photograph illustrating nano-sized QDs made in accordance with an embodiment of the present invention. This independently validates the sizes in FIGS. 9 and 10.

In further research, the inventors propose a novel, integrated biochemical, materials engineering and catalysis approach to further investigate nanoparticle biosynthesis in *S. maltophilia*. Such further research will have the following specific aims of: (1) Determining the exact composition and physical properties of metal precipitates generated by *S. maltophilia* (2) Identify optimal enzymes and growth conditions responsible for biosynthesis of selenium and cadmium nanostructures in *S. maltophilia* and other organisms; and (3) utilize the knowledge of structure, composition, and growth mechanism to generate semiconductor nanoparticles and nanostructures of pure and doped CdS and CdSe, including their photocatalytic activity for hydrogen generation via water dissociation. The inventors will continue to use their novel CdS and CdSe methods and systems as they further investigate the biosynthetic properties of *S. maltophilia*, as well as other organisms having tolerance to high concentrations of CdS, for example. The inventors have already shown that their methods render *S. maltophilia* capable of producing milligram-to-gram quantities of nanostructured materials from culture volumes on the order of 1-10 L. Media costs for growing *S. maltophilia* are on the order $1 per liter, which reduces the overall cost (on a per unit mass basis) by at least 100-fold relative to current chemical synthesis methods. Furthermore, high-density, continuous *S. maltophilia* growth can be achieved using a chemostat or fermenter, thereby eliminating the need for batch synthesis. Thus, the current, and future improved, inventive methods will produce highly monodisperse, inexpensive nanoparticles at a significant cost savings relative to current state-of-the art methods.

Reduced Environmental Impact—Most current approaches to reduce cost have focused on solvent recycling strategies to reduce synthesis costs. While this is effective in limiting consumption of coordinating and other solvents used during synthesis, this does not eliminate the requirement for volative, corrosive solvents and the generation of hazardous waste. In contrast, our method requires only aqueous solutions of growth media and metal salts, thereby eliminating the need for any coordinating solvents and hazardous waste. Thus, the inventors can achieve both a significant cost savings and environmental benefit using the proposed cellular biosynthetic methods.

Diversification of Novel Materials—One major advantage of in situ biosynthesis is the ability to apply directed evolution and genetic selection methods to generate novel nanostructured materials. The inventors can utilize flow cytometry and other high-throughput techniques to characterize the type and yield of nanostructured materials produced by individual cell variants within a population. With the ability to use recombinant DNA techniques to overexpress potential enzymes involved in biosynthesis, we have a method to engineering nanoparticle function through diversification of proteins involved in elemental metal reduction. Combining these two methods, the inventors have conceived the basis for a forward genetic selection method in which to generate large libraries of potential materials and select from this library based on absorbance, fluorescence or other material properties measured using flow cytometry. Thus, the invention is sufficiently flexible to enable us to rapidly generate and tailor materials for specific applications.

Furthermore, work is currently underway in the Berger and McIntosh laboratories aimed at the design, synthesis and characterization of mixed Cd and Se nanomaterials. They have demonstrated feasibility for the in situ synthesis of Se and Cd nanoparticles in *S. maltophilia*. This provides the foundation for further engineering and evolution of specific strains to design novel materials using the inventive methods herein. For example, as illustrated in FIG. 1, the inventive methods use forward- and side-scatter information from flow cytometry to distinguish cell populations with—and without nanoparticle synthesis capacity—increased side-scatter intensity is indicative of in situ nanoparticle synthesis.

Furthermore, the inventors correlate the signal from cell-based screens to determine median particle size in situ. As shown in FIG. 2, we are able to isolate nanoparticles from bacterial cells using direct lysis and centrifugation, and determine the average particle size via dynamic light scattering. There is a strong, positive correlation between the side-scatter intensity measured in situ from individual cells using flow cytometry and the in vitro particle size measured using DLS. Thus, the methods use in situ data collected from cell suspensions to guide the design and directed evolution of specific proteins to engineering specific materials. Obviously, FIGS. 1-10 demonstrate viability of the inventive methods using *S. maltophilia* to generate nanosized particles, such as CdS QDs.

A unique application of plasmid-based overexpression of specific enzymes responsible for in vivo biosynthesis of nanostructured materials is in directed evolution to generate potential novel materials with unique properties and compositions by flow cytometry. In particular, orthogonal ('side') scatter during sorting is proportional to the internal complexity or structure of the cell, and therefore can be used as a signature to correlate with more quantitative, detailed characterization methods. Our preliminary results (FIGS. 1*a-b* and 2) using selenium nanoparticles indicate that side-scatter intensity (SSC) in situ correlates with median particle size from purified nanoparticle samples using dynamic light scattering (DLS). Furthermore, mixed metal nanoparticles such as CdSe are capable of fluorescence (quantum dots or 'QDs'). Thus, in continuing validation and testing of the inventive methods herein, the inventors will evolve enzymes to generate mixed metal precipitates, which we can confirm using fluorescence to detect QD formation and increased SSC in terms of average particle size via flow cytometry.

Additional work is ongoing to fully identify composition and physical properties of metal precipitates generated by *S. maltophilia*. In order to fully determine the synthesis mechanism and the resulting photocatalytic activity, the inventors will characterize both bulk and surface chemistry and structure. For example, the band gap of the semiconductor particle is a function of the bulk structure and composition, while surface catalytic activity is dictated by surface structure and composition. The two can vary significantly. Thus, the inventors utilize dynamic light scattering (DLS) to determine nanoparticle size and solution stability, Aberration Corrected-High Angle Annular Dark Field Scanning Transmission Electron Microscopy (AC-HAADF STEM) to resolve particle shape and crystalline structure, and Scanning electron microscopy (SEM) to study nanostructures. The bulk average crystal structure will be determined by X-Ray Diffraction (XRD) and overall composition determined by Inductive Coupled Plasma-Mass Spectrometry (ICP-MS). These bulk techniques can be complemented with surface compositional analysis utilizing the new and unique High Sensitivity-Low Energy Ion Scattering (HS-LEIS) instrument.

The inventors also expect to apply the inventive methods to generate semiconductor nanoparticles and nanostructures of pure and doped CdS and CdSe, and understand their photocatalytic activity for hydrogen generation via water dissociation. For example, to generate mixed-metal nanoparticles and nanostructures, the inventors are pursuing two exemplary approaches. First, they will grow particles from a solution containing two metal precursors, for example, Cd and Se to form CdSe. It is expected this approach will yield particles with metals present in a ratio determined by the metabolic activity of *S. maltophilia* toward each metal. The second approach is to grow initial seed particles of one metal prior to switching the growth medium to one containing the second metal; this will likely lead to core-shell nanoparticles where a core of one material is coated in a shell of a second. Alternatively this may lead to Janus-like heterostructures where one 'face' of the particle is one material, and the other face is the second material. Core-shell and Janus-like particles are highly desirable as catalysts. By way of further example, FIG. 3 shows CdSe/CdS/Pt hetero nanostructures that have shown to be active for water dissociation. The surface photocatalytic activity of these particles is dictated by the underlying electronic structure. Thus a core of different material can lead to unique properties. The inventors can transform these particles into uniform compositions by careful annealing to facilitate atomic mixing while minimizing particle growth. Photocatalytic activity will be determined by placing the catalyst in water in an Ar purged sealed reactor before exposing to sunlight (a solar simulator with known light flux) for a set period. The rate of H2 generation will be determined by periodically sampling the head gas with a gas chromatograph equipped with a helium ionization detector to directly measure hydrogen concentration.

In some applications, the energy required to reduce both $CO_2$ and $H_2O$ will come directly from the absorption of a photon with energy greater than the semiconductor band gap. It is thus essential that the band gap be both wide enough to provide sufficient energy, and at the correct relative potential. FIG. 4 shows the band gap size and position for several potential semiconductors relative to the equilibrium potentials for the desired reactions. The minimum energy requirements for $H_2O$ and $CO_2$ reduction are 1.229 and 1.33 eV, respectively, setting a minimum for the semiconductor band gap. However, we require significantly more energy than this minimum due to kinetic and entropic losses. A practical target band gap is suggested to be ~2.4 eV, corresponding to electromagnetic radiation of wavelength 516 nm or shorter. It is this required band gap that sets the fraction of the energy in the incoming light that can be collected, namely ~26% based on a semiconductor having a band gap of 2.4 eV. Minimizing kinetic losses can theoretically increase the fraction of light that can be harvested by allowing us to use a material with a band gap smaller than 2.4 eV. However, we can never go below the thermodynamic energy requirement of 1.33 eV for $CO_2$ reduction. Conversely, the product yields can be increased by providing substantial energy above the 1.229 and 1.33 eV minima. Higher overpotentials drive the reaction at higher rates, as suggested by the higher rates of $CO_2$ reduction observed over SiC (band gap 3.0 eV) when compared with other materials. Thus there is a trade-off. Higher band gap leads to higher rates, but a lower fraction of the solar spectrum that can be captured. In addition to the magnitude of the band gap, the band gap position relative to the desired reaction potentials is critical—the band gap must span the desired reaction potentials in order to provide the energy for reaction.

For bulk semiconductors, the band gap energy and position are fixed. However, reduction of the semiconductor particle size to the length scale below the exciton Bohr radius, leads to quantum confinement effects and a progressive increase of the band gap with decreasing particle size. Thus the band gap energy for the resulting QDs can be tuned based on particle size and shape. This tuning of the band gap enables us to utilize QDs of various sizes to supply controlled overpotentials (energy above the required thermodynamic minimum) to the reaction system. Thus we can find an optimum position on the band gap vs. rate curve by varying the QD size while maintaining all other system parameters constant. Due to their small size, the diffusion length for the generated excitons to the surface is extremely small. Thus QDs offer a means to utilize the generated excitons through surface reaction or charge transfer prior to their recombination. In particular, QDs offer high quantum yields (fraction of light with energy above the bandgap that is captured and utilized), and high surface areas for reaction.

CdS is a feasible material for $CO_2$ reduction in terms of band position and sufficient band gap energy (2.4 eV for the bulk material and 3.55 eV (349 nm) for 2 nm QDs). $CO_2$ reduction to formic acid and MeOH and C2 species has previously been reported using bulk CdS. The large band gap for CdS QDs results in utilization of only a small fraction (~3%) of the solar flux. In order to maximize the system efficiency, we require QDs with band gaps closer to 2.4 eV. CdSe QDs meet this requirement at a diameter of ~3 nm. Thus, we can supply sufficient energy to the reaction with CdSe QDs at or below this size.

We have initially selected the sulfide and selenide family of semiconductors in order to focus our efforts and to meet the goal of developing an exemplary commercializable low-cost, high efficiency, biosynthetic route to commercial-scale QD production. Based on the above considerations and our initial success in large-scale CdS QD biosynthesis, we will utilize CdS and CdSe QDs in order to reach our project goals. Our current biosynthetic CdS QD process will be expanded to CdSe, and we anticipate that Se utilization will follow a similar biological pathway to sulfur utilization in the bacteria based on previous studies.

Bio-inspired Benign Fabrication of QDs. Current QD synthesis approaches include sol, micellar, sol-gel, precipitation, pyrolysis, hydrothermal, and vapor deposition methods. Each of these approaches requires organic solvents such as chloroform for QD solubilization, expensive capping reagents to promote QD water solubility. Additionally, the labor-intensive multi-step chemical synthesis route (nucleation, capping, purification) to QD production reduces the recovery of soluble, purified QDs. These factors combine to yield costs for commercial-scale QD production in the range of $4500/g for CdS (Sigma Aldrich). For comparison, the raw material cost of Cd acetate is $400/kg (Sigma Aldrich), which indicates the major drawback to wide-scale use of CdS QDs lies not in raw material costs, but rather developing cost-effective routes to large-scale synthesis and purification.

The inventors have conceived and reduced to practice a disruptive new approach to QD production through bacterial biosynthesis, which enables high-yield, extracellular synthesis of water-soluble CdS and CdSe QDs from batch culture with precise control over QD size. FIGS. 5-11 illustrate the innovative aspects of this process.

A key advantage of the inventive methods herein is their compatibility with direct fermentation. That compatibility enables direct conversion from laboratory (batch shake-flask) to pilot (continuous fermentation) scale production of QDs, thereby achieving higher yields as well as rates of QD production. For example, the inventors are now pursuing a 10 L, pilot-scale, continuous-flow bioreactor system, which includes pH, cell density (optical density), dissolved $O_2$ and agitation control. Additionally, we have pursued a diode-array UV-visible spectrophotometric detector, which can be used to monitor extracellular QD production directly in culture broth. The certain feasibility of this scale-up is demonstrated based upon the knowledge of the inventors as one skilled in the art, and as proven by undergraduate students under the supervision of the inventors producing 1 L of 1.7 nm CdS QD culture supernatants pooled from multiple 100 mL batches. While full commercial production will require continuous processing, multiple batches (we estimate 500 mL batch size to be feasible), our approach will enable production sufficient to match the QD production system within a university environment.

Continuing field trials will be conducted on the Lehigh University campus. A 10 L pilot scaled system will be manufactured and filled with a photocatalysts suspension optimized from the laboratory experiments. This system will operate under pressure (5 atm), to enhance $CO_2$ solubility in the aqueous media, with a constant supply of $CO_2$ to maintain this pressure head. Fuel production will be measured periodically over a period of two weeks. The incident solar radiation during this period will be measured utilizing a pyreheliometer to enable calculation of the system efficiency as a function of time. Product production rates will be measured by GC as for the laboratory scale system. Successful completion of this work is expected to confirm the inventor's conception in a commercial-scale operating environment and process, and will clearly demonstrate the commercial feasibility of the methods and systems described herein. Nonetheless, the invention as claimed is complete, and enabled to anyone skilled in the art.

By way of non-limiting disclosure, the inventors have examined bacteria that have proven useful with the inventions herein. For example, as illustrated in FIG. 22, Genotyping of a environmental *S. maltophilia* isolate (later identified and assigned reference LU08) was performed. Individual colonies of *S. maltophilia* were selectively isolated from environmental (soil) samples using previously described methods using imipenem and DL-methionine (Bollet et al., 1995). The strains were identified using colony PCR for specific gene products and confirmed using 16S PCR sequencing with 'universal' primers as described previously for bacterial identification (DOI 10.1128/JCM.01228-07).

The following genetic information, represented as including sequence listings as illustrated in FIGS. 12-21, was discovered for several such exemplary bacteria.

```
Genotyping of environmental S. maltophilia - Variant 5 (LHU-5-
CP1).
TGCAGTCGAACGGCAGCACAGGAGAGCTTGCTCTCTGGGTGGCGA

GTGGCGGACGGGTGAGGAATACATCGGAATCTACTTTTTCGTGGGGGATAAC

GTAGGGAAACTTACGCTAATACCGCATACGACCTACGGGTGAAAGCAGGGG

ATCTTCGGACCTTGCGCGATTGAATGAGCCGATGTCGGATTAGCTAGTTGGCG

GGGTAAAGGCCCACCAAGGCGACGATCCGTAGCTGGTCTGAGAGGATGATCA

GCCACACTGGAACTGAGACACGGTCCAGACTCCTACGGGAGGCAGCAGTGG

GGAATATTGGACAATGGGCGCAAGCCTGATCCAGCCATACCGCGTGGGTGAA

GAAGGCCTTCGGGTTGTAAAGCCCTTTTGTTGGGAAANAAANCCAGCNGGTT

AANACCCGGTTGGGANGACGGTACCCNAAGAATAAGCACCNNCNANNTTCA

NGCCNNCA.

Genotyping of environmental S. maltophilia isolate - Variant 5
(LHU-5-CP2)
CGTCNTCCCNACCGGGTATTAACCAGCTGGATTTCTTTCCCAACAA

AAGGGCTTTACAACCCGAAGGCCTTCTTCACCCACGCGGTATGGCTGGATCA

GGCTTGCGCCCATTGTCCAATATTCCCCACTGCTGCCTCCCGTAGGAGTCTGG

ACCGTGTCTCAGTTCCAGTGTGGCTGATCATCCTCTCAGACCAGCTACGGATC

GTCGCCTTGGTGGGCCTTTACCCCGCCAACTAGCTAATCCGACATCGGCTCAT

TCAATCGCGCAAGGTCCGAAGATCCCCTGCTTTCACCCGTAGGTCGTATGCG

GTATTAGCGTAAGTTTCCCTACGTTATCCCCCACGAAAAAGTAGATTCCGATG

TATTCCTCACCCGTCCGCCACTCGCCACCCAGAGAGCAAGCTCTCCTGTGCTG

CCGTTCGACTTGCANGTGTTAGGCCTACCGCCAGCGTTCACTCTNANCCAGG

ATCAANCTCTCCAA.

Genotyping of environmental S. maltophilia isolate - Variant 4
(LHU-4-CP1)
NACNCNNGCAGTCGAACGGCAGCACAGGANAGCTTGCTCTCTGGG

TGGCGAGTGGCGGNCGGGTGAGGAATACATCGGAATCTACTTTTTCGTGGGG

GATAACGTAGGGAAACTTACGCTAATACCGCATACGACCTACGGGTGAAAGC

AGGGGATCTTCGGACCTTGCGCGANTGAATGAGCCNATGTCGGANTANCNNN

NNGGNGGGNNNNNNGNCCACCANNGC.

Genotyping of environmental S. maltapliilia isolate - Variant 4
(LHU-4-CP2).
TNNGGNNGTCNTCCCNACCGGGTATTAACCAGCTGGATTTCTTTCC

CAACAAAAGGGCTTTACAACCCGAAGGCCTTCTTCACCCACGCGGTATGGCT

GGATCAGGCTTGCGCCCATTGTCCAATATTCCCCACTGCTGCCTCCCGTAGGA

GTCTGGACCGTGTCTCAGTTCCAGTGTGGCTGATCATCCTCTCAGACCAGCTA
```

-continued

CGGATCGTCGCCTTGGTGGGCCTTTACCCCGCCAACTAGCTAATCCGACATCG

GCTCATTCAATCGCGCAAGGTCCGAAGATCCCCTGCTTTCACCCGTAGGTCGT

ATGCGGTATTAGCGTAAGTTTCCCTACGTTATCCCCCACGAAAAAGTAGATTC

CGATGTATTCCTCACCCGTCCGCCACTCGCCACCCAGAGAGCAAGCTCTCCTG

TGCTGCCGTTCGACTTGCATGTGTTAGGCCTACCGCCAGCGTTCACTCTGAGC

NAGGATCAAACTCTCCAAN.

Genotyping of environmental *S. maltophilia* isolate - Variant 3 (LHU-3-CP1).

NCNTGCAGTCGNCGGCAGCACAGGAGAGCTTGCTCTCTGGGTGGC

GAGTGGCGGACGGGTGAGGAATACATCGGAATCTACTTTTTCGTGGGGGATA

ACGTAGGGAAACTTACGCTAATACCGCATACGACCTACGGGTGAAAGCAGGG

GATCTTCGGACCTTGCGCGATTGAATGAGCCGATGTCGGATTAGCTAGTTGGC

GGGGTAAAGGCCCACCAAGGCGACGATCCGTAGCTGGTCTGAGAGGATGATC

AGCCACACTGGAACTGAGACACGGTCCAGACTCCTACGGGAGGCAGCAGTG

GGGAATATTGGACAATGGGCGCAA GCCTGATCCAGCCATACCGCGTGGGTGA

AGAAGGCCTTCGGGTTGTAAAGCCCTTTTGTTGGGAAAGAAATCCAGCTGGT

TAATACCCGGTTGGGATGACGGTACCCAAAGAATAAGCACCGGCTAACTTCN

NGCCAGCNNNNNCGGTAATANANNTTNT.

Genotyping of environmental *S. maltophilia* isolate - Variant 3 (LHU-3-CP2).

TCNTCCCNACCGGGTATTAACCAGCTGGANTTCTTTCCCAACAAAA

GGGCTTTACAACCCGAAGGCCTTCTTCACCCACGCGGTATGGCTGGATCAGG

CTTGCGCCCATTGTCCAATATTCCCCACTGCTGCCTCCCGTAGGAGTCTGGAC

CGTGTCTCAGTTCCAGTGTGGCTGATCATCCTCTCAGACCAGCTACGGATCGT

CGCCTTGGTGGGCCTTTACCCCGCCAACTAGCTAATCCGACATCGGCTCATTC

AATCGCGCAAGGTCCGAAGATCCCCTGCTTTCACCCGTAGGTCGTATGCGGT

ATTAGCGTAAGTTTCCCTACGTTATCCCCCACGAAAAAGTAGATTCCGATGTA

TTCCTCACCCGTCCGCCACTCGCCACCCAGAGAGCAAGCTCTCCTGTGCTGCC

GTTCGACTTGCATGTGTTAGGCCTACCGCCAGCGTTCACTCTNANCCNNGANC

AAACTCTCCN.

Genotyping of environmental *S. maltophilia* isolate - Variant 2 (LHU-2-CP1).

CNTGCNAGTCGAACGGCAGCACAGGAGAGCTTGCTCTCTGGGTGG

CGAGTGGCGGACGGGTGAGGAATACATCGGAATCTACTTTTTCGTGGGGGAT

AACGTAGGGAAACTTACGCTAATACCGCATACGACCTACGGGTGAAAGCAGG

GGATCTTCGGACCTTGCGCGATTGAATGAGCCGATGTCGGATTAGCTAGTTG

GCGGGGTAAAGGCCCACCAAGGCGACGATCCGTAGCTGGTCTGAGAGGATG

ATCAGCCACACTGGAACTGAGACACGGTCCAGACTCCTACGGGAGGCAGCA

GTGGGGAATATTGGACAATGGGCGCAAGCCTGATCCAGCCATACCGCGTGGG

TGAAGAAGGCCTTCGGGTTGTAAAGCCCTTTTGTTGGGAAAGAAATCCAGCT

GGTTAATACCCGGTTGGGATGACGGTACCCAAAGAATAAGCACCGGCTAACT

TCNNGCCAGCNNNNNNGGTAAT.

Genotyping of environmental *S. maltophilia* isolate - Variant 2 (LHU-2-CP2).
GTCNTCCCNACCGGGTATTAACCAGCTGGATTTCTTTCCCAACAAA

AGGGCTTTACAACCCGAAGGCCTTCTTCACCCACGCGGTATGGCTGGATCAG

GCTTGCGCCCATTGTCCAATATTCCCCACTGCTGCCTCCCGTAGGAGTCTGGA

CCGTGTCTCAGTTCCAGTGTGGCTGATCATCCTCTCAGACCAGCTACGGATCG

TCGCCTTGGTGGGCCTTTACCCCGCCAACTAGCTAATCCGACATCGGCTCATT

CAATCGCGCAAGGTCCGAAGATCCCCTGCTTTCACCCGTAGGTCGTATGCGG

TATTAGCGTAAGTTTCCCTACGTTATCCCCCACGAAAAAGTAGATTCCGATGT

ATTCCTCACCCGTCCGCCACTCGCCACCCAGAGAGCAAGCTCTCCTGTGCTGC

CGTTCGACTTGCATGTGTTAGGCCTACCGCCAGCGTTCACTCTNNNNCNNGAT

CNNACTCTCCAAAA.

Genotyping of environmental *S. maltophilia* isolate - Variant 1 (LHU-1-CP1).
NNTGCAGTCGAACGGCAGCACAGGAGAGCTTGCTCTCTGGGTGGC

GAGTGGCGGACGGGTGAGGAATACATCGGAATCTACTTTTTCGTGGGGGATA

ACGTAGGGAAACTTACGCTAATACCGCATACGACCTACGGGTGAAAGCAGGG

GATCTTCGGACCTTGCGCGATTGAATGAGCCGATGTCGGATTAGCTAGTTGGC

GGGGTAAAGGCCCACCAAGGCGACGATCCGTAGCTGGTCTGAGAGGATGATC

AGCCACACTGGAACTGAGACACGGTCCAGACTCCTACGGGAGGCAGCAGTG

GGGAATATTGGACAATGGGCGCAAGCCTGATCCAGCCATACCGCGTGGGTGA

AGAAGGCCTTCGGGTTGTAAAGCCCTTTTGTTGGGAAAGAAATCCAGCTGGT

TAATACCCGGTTGGGATGACGGTACCCAAAGAATAAGCACCGGCTAACTNNN

TGCNANNNGCCNNNGTAATNN.

Genotyping of Environmental *S. maltophilia* Isolate.

Individual colonies of *S. maltophilia* were selectively isolated from environmental (soil) samples using previously described methods using imipenem and DL-methionine (Ballet et al., 1995). The initial useful strains (designated herein as LU08) were identified using colony PCR for specific gene products and confirmed using 16S PCR sequencing with 'universal' primers as described previously for bacterial identification (DOI 10.1128/JCM.01228-07). The resulting sequence listing was determined (though, as previously described herein, evolution of the strain occurs during growth, and the sequence listings herein are therefore not intended to limit the invention herein).

GGGATAACGTAGGGAAACTTACGCTAATACCGCATACGACCTACG

GGTGAAAGCAGGGGATCTACGGACCTTGCGCGATTGAATGAGCCGATGTC

GGATTAGCTAGTTGGCGGGGTAAAGGCCCACCAAGGCGACGATCCGTAGC

TGGTCTGAGAGGATGATCAGCCACACTGGAACTGAGACACGGTCCAGACT

CCTACGGGAGCCAGCAGTGGGGAATATTGGACAATGGGCGCAAGCCTGAT

CCAGCCATACCGCGTGGGTGAAGAAGGCCTTCGGGTTGTAAAGCCCTTTT

CTTGGGAAAGAAATCCAGCTGGTTAATACCCGGTTGGGATGACGGTACCC

AAAGAATAAGCACCGGCTAACTTCGTGCCAGCAGCCGCGGTAATACGAAG

GGTGCAAGCGTTACTCGGAATTACTGGGCGTAAAGCGTGCGTAGGTGGTT

-continued

GTTTAAGTCTGTTGTGAAAGCCCTGGGCTCAACCTGGGAACTGCAGTGGA

AACTGGACGACTAGAGTGTGGTAGAGGGTAGCGGAATTCCTGGTGTAGCA

GTGAAATGCGTAGAGATCAGGAGGAACATCCATGGCGAAGGCAGCTACCT

GGACCAAGACTGACACTGAGGCACGAAAGCGTGGGGAGCAAACAGGATTA

GATACCCTGGTAGTCCACGCCCTAAACGATGCGAACTGGATGTTGGGTGC

AATTTGGCACGCAGTATCGAAGCTAACGCGTTAAGTTCGCCGCCTGGGGA

GTACGGTCGCAAGACTGAAACTCAAAGGAATTGACGGGGGCCCGCACAAG

CGGTGGAGTATGTGGTATAATTCGATGCAACGCGAAGAACCTTACCTGGC

CTTGACATCTCGAGAACTTTCCAGAGATGGATTGGTGCCTTCGGGAACTC

GAACACAGGTGCTGCATGGCTGTCGTCAGCTCGTGTCGTGAGATGTTGGG

TTAAGTCCCGCAACGAGCGCAACCCTTGTCCTTAGTTGCCAGCACGTAAT

GGTGGGAACTCTAAGGAGACCGCCGGTGACAAACCGGAGGAAGGTGGGGA

TGACGTCAAGACATCATGGCCCTTACGGCCAGGGCTACACACGTACTACA

ATGGTAGGGACAGAGGGCTGCAAGCCGGCGACGGTAAGCCAATCCCAGAA

ACCCTATCTCAGTCCGGATTGGAGTCTGCAACTCGACTCCATGAAGTCGG

```
                               -continued
AATCGCTAGTAATCGCAGATCAGCATTGCTGCGGTGAATACGTTCCCGGG

CCTTGTACACACCGCCCGTCACACCATGGGAGTTT.

F1; AGAGTTTGATCCTGGCTCAG.

R1; GGTTACCTTGTTACGACTT
```

List of references used herein: Bai, H., Zhang, Z., Guo, Y., and Jia, W. (2009a). Biological Synthesis of Size-Controlled Cadmium Sulfide Nanoparticles Using Immobilized *Rhodobacter* sphaeroides. Nanoscale Res Lett 4, 717-723; Bai, H. J., Zhang, Z. M., Guo, Y., and Yang, G. E. (2009b); Biosynthesis of cadmium sulfide nanoparticles by photosynthetic bacteria *Rhodopseudomonas* palustris. Colloids and Surfaces B-Biointerfaces 70, 142-146; Baskoutas, S., and Terzis, A. F. (2006). Size-dependent band gap of colloidal quantum dots. Journal of Applied Physics 99, 013708; Bera, D., Qian, L., Tseng, T.-K., and Holloway, P. H. (2010). Quantum Dots and Their Multimodal Applications: A Review. Materials 3, 2260-2345; Boatman, E., Lisensky, G., and Nordell, K. (2005). A Safer, Easier, Faster Synthesis for CdSe Quantum Dot Nanocrystals. Journal of Chemical Education 82, 3; Chien, C., Hung, C., and Han, C. (2007). Removal of cadmium ions during stationary growth phase by an extremely cadmium-resistant strain of *Stenotrophomonas* sp. Environmental toxicology and chemistry 26, 664-668; Dungan, R. S., Yates, S. R., and Frankenberger, W. T. (2003). Transformations of selenate and selenite by *Stenotrophomonas maltophilia* isolated from a seleniferous agricultural drainage pond sediment. Environmental Microbiology 5, 287-295; Green, M. R., and Sambrook, J. (2012). Molecular cloning: a laboratory manual, 4th edn (Cold Spring Harbor, N.Y., Cold Spring Harbor Laboratory Press); Kang, S. H., Bozhilov, K. N., Myung, N. V., Mulchandani, A., and Chen, W. (2008). Microbial Synthesis of CdS Nanocrystals in Genetically Engineered *E. coli*. Angewandte Chemie International Edition 47, 5186-5189; Mi, C., Wang, Y., Zhang, J., Huang, H., Xu, L., Wang, S., Fang, X., Fang, J., Mao, C., and Xu, S. (2011). Biosynthesis and characterization of CdS quantum dots in genetically engineered *Escherichia coli*. Journal of Biotechnology 153, 125-132; Neeleshwar, S., Chen, C., Tsai, C., Chen, Y., Chen, C., Shyu, S., and Seehra, M. (2005). Size-dependent properties of CdSe quantum dots. Physical Review B 71; Pages, D., Rose, J., Conrod, S., Cuine, S., Carrier, P., Heulin, T., and Achouak, W. (2008). Heavy Metal Tolerance in *Stenotrophomonas maltophilia*. PLoS ONE 3, e1539; Pal, D., Stoleru, V. G., Towe, E., and Firsov, D. (2002). Quantum Dot-Size Variation and Its Impact on Emission and Absorption Characteristics: An Experimental and Theoretical Modeling Investigation. Japanese Journal of Applied Physics 41, 482-489; Sweeney, R., Mao, C., Gao, X., Burt, J. L., Belcher, A. M., Georgiou, G., and Iverson, B. L. (2004). Bacterial Biosynthesis of Cadmium Sulfide Nanocrystals. Chemistry & Biology 11, 1553-1559; Yadav, V., Sharma, N., Prakash, R., Raina, K. K., Bharadwaj, L. M., and Prakash, N. T. (2008). Generation of Selenium containing Nano-structures by soil bacterium, *Pseudomonas aeruginosa*. Biotechnology 7, 299-304; Yu, W., Qu, L., Guo, W., and Peng, X. (2003). Experimental determination of the extinction coefficient of CdTe, CdSe, and CdS nanocrystals. Chemistry of Materials 15, 2854-2860.

While the principles of the invention have been described above in connection with preferred embodiments, it is to be clearly understood that this description is made only by way of example and not as a limitation of the scope of the invention.

The invention claimed is:

1. A biosynthetic method of making semiconductor quantum dots (sQDs) comprising:
providing a selected bacterial strain that is adapted for tolerance to a selected metal salt and producing sQDs when grown in a growth culture medium comprising said selected metal salt;
placing the selected bacterial strain in an aerobic fluid culture and inducing production of controlled size sQDs by growing the selected bacterial strain in the growth culture medium comprising the selected metal salt for a time sufficient for the selected bacterial strain to utilize the selected metal salt to assemble sQDs and extracellularly release the sQDs into the growth culture medium,
harvesting the sQDs from a cell-free supernatant of the growth culture medium after a time sufficient to produce the sQDs having an optical property,
wherein the selected bacterial strain is a member of Genus Stenotrophomonas and is selected from the group consisting of: Stenotrophomonas (S.) acidaminiphila, S. dokdonensis, S. koreensis, S. maltophilia, S. nitritireducens, and S. rhizophila, and wherein the growth culture medium includes the selected metal salt at a concentration above 0.1 mM and further includes L-cysteine.

2. The method of claim 1, wherein the sQDs have an average particle size of between about 1 nm to about 10 nm.

3. The method of claim 1, wherein the selected bacterial strain is a member of Order Xanthomonadales.

4. The method of claim 1, wherein the aerobic fluid culture is run as a continuous process.

5. The method of claim 1, wherein the selected metal salt is a member of one or more of I-VI, II-VI, IV-VI and III-V semiconductor metal groups.

6. The method of claim 5, wherein the selected metal salt comprises cadmium, and wherein the selected bacterial strain is tolerant to elevated cadmium concentrations.

7. The method of claim 1, wherein the selected bacterial strain has been adapted by iterative growth steps in increasing aqueous concentrations of the selected metal salt with selection at each growth step for absorbance spectrum and spontaneous luminescence of the sQDs.

8. The method of claim 1, wherein the selected bacterial strain has been adapted by plasmid transformation and selection of the bacterial strain for growth in an increased aqueous concentration of the selected metal salt, whereby absorbance spectrum and spontaneous luminescence of the sQDs is obtained.

9. The method of claim 1, wherein the growth culture medium includes a cadmium (Cd) salt and a selenium (Se) salt and the selected bacterial strain produces CdSe sQDs.

10. A biosynthetic method of making mixed metal core-shell Quantum Dots (QDs) comprising:
providing a selected bacterial strain that is tolerant to an elevated concentration of a salt of a first selected metal, said selected bacterial strain is induced to produce QDs when grown in the elevated concentration of the salt of said first selected metal;
placing the selected bacterial strain in an aerobic fluid culture and inducing production of initial seed particles of core QDs by growing the selected bacterial strain in a growth culture medium comprising the elevated concentration of the first selected metal salt for a time sufficient for the selected bacterial strain to utilize the first selected metal salt to assemble core QDs comprising the first selected metal salt and extracellularly release the core QDs into the growth culture medium, switching the growth culture medium to a second growth culture medium comprising a salt of a second selected metal and growing the bacterial strain in said second growth culture medium for a time sufficient for the selected bacterial strain to assemble shell QDs comprising said second metal salt and extracellularly release the shell QDs into the growth culture medium whereby the shell QDs coat the core QDs to form mixed metal core-shell QDs, and
harvesting the mixed metal core-shell QDs from a cell-free supernatant of the growth culture medium;
wherein the elevated concentration of said first and said second metal salts is 0.1 mM, and
the selected bacterial strain is a species selected from the group consisting of: Stenotrophomonas (S.) acidaminiphila, S. dokdonensis, S. koreensis, S. maltophilia, S. nitritireducens, and S. rhizophila.

11. The method of claim 10, wherein the selected bacterial strain has been selected for tolerance to an elevated concentration of the first selected metal salt by iterative growth steps in increasing aqueous concentrations of the selected metal salt with selection at each growth step for absorbance spectrum and spontaneous luminescence of the QDs.

* * * * *